(12) United States Patent
Kitamura et al.

(10) Patent No.: US 11,961,276 B2
(45) Date of Patent: Apr. 16, 2024

(54) LINEAR STRUCTURE EXTRACTION DEVICE, METHOD, PROGRAM, AND LEARNED MODEL

(71) Applicant: FUJIFILM Corporation, Tokyo (JP)

(72) Inventors: Yoshiro Kitamura, Tokyo (JP); Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 17/477,547

(22) Filed: Sep. 17, 2021

(65) Prior Publication Data

US 2022/0004797 A1  Jan. 6, 2022

Related U.S. Application Data

(63) Continuation of application No. PCT/JP2020/013334, filed on Mar. 25, 2020.

(30) Foreign Application Priority Data

Mar. 29, 2019 (JP) ................................ 2019-066982

(51) Int. Cl.
  *G06V 10/44* (2022.01)
  *A61B 6/50* (2024.01)
  (Continued)

(52) U.S. Cl.
  CPC .............. *G06V 10/44* (2022.01); *A61B 6/504* (2013.01); *G06F 18/213* (2023.01);
  (Continued)

(58) Field of Classification Search
  None
  See application file for complete search history.

(56) References Cited

U.S. PATENT DOCUMENTS 9,858,496 B2  1/2018  Sun et al.
10,198,671 B1  2/2019  Yang et al.
(Continued)

FOREIGN PATENT DOCUMENTS

JP  2018534694  11/2018
JP  2019500110  1/2019
WO  2018165753  9/2018

OTHER PUBLICATIONS

Shaoqing Ren et al., "Faster R-CNN: Towards Real-Time Object Detection with Region Proposal Networks," arXiv:1506.01497 [cs.CV], Jan. 2016, pp. 1-14.
(Continued)

*Primary Examiner* — Leon Flores
(74) *Attorney, Agent, or Firm* — JCIPRNET

(57) ABSTRACT

Provided are a linear structure extraction device, a method, a program, and a learned model which can detect a linear structure in an image. A linear structure extraction device according to an embodiment of the present disclosure includes a learning model that is learned to receive an input of the image and output, as a prediction result, one or more element points which constitute the linear structure from the image, in which the learning model includes a first processing module that receives the image and generates a feature map representing a feature amount of the image by convolution processing, and a second processing module that calculates a shift amount from a unit center point to the element point of the linear structure closest to the unit center point, for each unit obtained by dividing the feature map into a plurality of the units including regions having a predetermined size in a grid pattern.

20 Claims, 19 Drawing Sheets

(51) Int. Cl.
*G06F 18/213* (2023.01)
*G06F 18/214* (2023.01)
*G06F 18/2431* (2023.01)
*G06T 3/4046* (2024.01)
*G06T 7/00* (2017.01)
*G06V 10/25* (2022.01)
*G06V 10/94* (2022.01)

(52) U.S. Cl.
CPC ........ *G06F 18/214* (2023.01); *G06F 18/2431* (2023.01); *G06T 3/4046* (2013.01); *G06T 7/0012* (2013.01); *G06V 10/25* (2022.01); *G06V 10/95* (2022.01); *G06T 2207/20081* (2013.01); *G06T 2207/20084* (2013.01); *G06T 2207/30101* (2013.01); *G06V 2201/03* (2022.01)

(56) References Cited

U.S. PATENT DOCUMENTS

2017/0124415 A1 5/2017 Choi et al.
2017/0258433 A1* 9/2017 Gulsun ................ A61B 6/5217
2018/0365824 A1 12/2018 Yuh et al.
2019/0019287 A1* 1/2019 Reda .................... G06V 10/764

OTHER PUBLICATIONS

Gahyun Suh et al., "Deep faster R-CNN-based automated detection and localization of multiple types of damage," Sensors and Smart Structures Technologies for Civil, Mechanical, and Aerospace Systems, Mar. 2018, pp. 1-9.

"International Search Report (Form PCT/ISA/210) of PCT/JP2020/013334," dated Jun. 23, 2020, with English translation thereof, pp. 1-5.

"Written Opinion of the International Searching Authority (Form PCT/ISA/237)" of PCT/JP2020/013334, dated Jun. 23, 2020, with English translation thereof, pp. 1-7.

Shaoqing Ren et al., "Faster R-CNN: Towards Real-Time Object Detection with Region Proposal Networks," Advances in Neural Information Processing Systems 28 (NIPS 2015), Jun. 2015, pp. 1-9.

"Search Report of Europe Counterpart Application", dated Apr. 25, 2022, p. 1-p. 9.

* cited by examiner

LINEAR STRUCTURE EXTRACTION DEVICE, METHOD, PROGRAM, AND LEARNED MODEL

CROSS-REFERENCE TO RELATED APPLICATIONS

The present application is a Continuation of PCT International Application No. PCT/JP2020/013334 filed on Mar. 25, 2020 claiming priority under 35 U.S.C § 119(a) to Japanese Patent Application No. 2019-066982 filed on Mar. 29, 2019. Each of the above applications is hereby expressly incorporated by reference, in its entirety, into the present application.

BACKGROUND OF THE INVENTION

1. Field of the Invention

The present invention relates to a linear structure extraction device, a method, a program, and a learned model, and particularly relates to an image processing technique and a machine learning technique of detecting a linear target object in an image.

2. Description of the Related Art

As an algorithm for detecting an object by using deep learning, in U.S. Pat. No. 9,858,496B and Ren, Shaoqing, et al. "Faster R-CNN: Towards real-time object detection with region proposal networks." Advances in neural information processing systems. 2015, a method called Faster region-based convolutional neural networks (R-CNN) is proposed. In Gahayun Suh, Young-Jin Cha "Deep faster R-CNN-based automated detection and localization of multiple types of damage" Sensors and Smart Structures Technologies for Civil, Mechanical, and Aerospace Systems 2018, a method for automatically detecting a deteriorated portion of a structure, such as rust on iron, peeling, corrosion of a bolt, and a crack in concrete, from images of a bridge and a building by using Faster R-CNN is proposed.

SUMMARY OF THE INVENTION

The crack in the concrete is a form of an object that has a linear structure. Another example of the object that has the linear structure is a tubular structure, such as a blood vessel or bronchus in a medical image. In U.S. Pat. No. 9,858,496B and Ren, Shaoqing, et al. "Faster R-CNN: Towards real-time object detection with region proposal networks." Advances in neural information processing systems. 2015, an application method for detecting the linear structure from the image is not disclosed. For detecting the linear structure, it is conceivable to detect a linear object from the image by an image segmentation method. However, for the machine learning for realizing a task of image segmentation, a large number of images with correct labels for a pixel unit is required, and thus creation of such correct images is difficult.

In Gahayun Suh, Young-Jin Cha "Deep faster R-CNN-based automated detection and localization of multiple types of damage" Sensors and Smart Structures Technologies for Civil, Mechanical, and Aerospace Systems 2018, the Faster R-CNN algorithm is applied as it is to the crack in concrete, and a bounding box including the crack is continuously detected in the image. In this case, a detection result is a rectangular region indicated by the bounding box, and it is difficult to perform reconstruction processing of specifying a center line or the like representing a region of the linear object from the detection result output as such a group of the rectangular regions.

The present invention has been made in view of such circumstances, and is to provide a linear structure extraction device, a method, a program, and a learned model which can detect a linear structure in an image.

An aspect of the present disclosure relates to a linear structure extraction device that extracts element points which constitute a linear structure from an image, the device comprising a learning model that is learned to receive an input of the image and output, as a prediction result, one or more element points which constitute the linear structure from the image, in which the learning model includes a first processing module that receives the image and generates a feature map representing a feature amount of the image by convolution processing, and a second processing module that calculates a shift amount from a unit center point to the element point of the linear structure closest to the unit center point, for each unit obtained by dividing the feature map into a plurality of the units including regions having a predetermined size in a grid pattern.

In the linear structure extraction device according to another aspect of the present disclosure, the second processing module may dispose anchors, which are one or more reference shape regions having predetermined shape and size, in each of the units, and may perform, for each unit, the convolution processing by using the feature amount at a position of the unit to calculate the shift amount for moving an anchor center point of the anchor to a closest point, which is the element point of the linear structure closest to the anchor center point, and a score for determining whether or not the linear structure is present in the anchor.

In the linear structure extraction device according to still another aspect of the present disclosure, the reference shape region may be a rectangular region in a case in which the image is a two-dimensional image, and may be a rectangular parallelepiped region in a case in which the image is a three-dimensional image.

In the linear structure extraction device according to still another aspect of the present disclosure, the linear structure may be a representative line of a region having a thickness in the image, and a plurality of the anchors having different sizes may be used in accordance with the thickness of the region having the thickness.

In the linear structure extraction device according to still another aspect of the present disclosure, the linear structure may be a representative line of a region having a thickness in the image, and the second processing module may be learned to change the size of the anchor in accordance with the thickness of the region having the thickness, which is a target.

In the linear structure extraction device according to still another aspect of the present disclosure, the linear structure may be a representative line of a region having a thickness in the image, and the second processing module may be learned to calculate, for each anchor, a deformation magnification of the anchor in a direction of at least one side of the anchor in accordance with the thickness of the region having the thickness around the closest point.

In the linear structure extraction device according to still another aspect of the present disclosure, the region having the thickness may be a tubular structure, and the representative line may be a center line along a route of the tubular structure.

In the linear structure extraction device according to still another aspect of the present disclosure, each of the first processing module and the second processing module may be configured by a neural network, the first processing module may be configured by a convolutional neural network including a plurality of convolutional layers, and the second processing module may include a convolutional layer different from that of the first processing module and be configured by a region proposal network that predicts a candidate region including the linear structure from the feature map.

The linear structure extraction device according to still another aspect of the present disclosure may further comprise a third processing module that is learned to perform classification of each point with respect to the element points of the linear structure predicted by the second processing module.

In the linear structure extraction device according to still another aspect of the present disclosure, a class classified by the third processing module may include at least one of a root, a branch, a tip, or a point on a twig in a tree structure of graph theory.

In the linear structure extraction device according to still another aspect of the present disclosure, the linear structure may be a center line along a route of a blood vessel, and a class classified by the third processing module may include a specific anatomical name in a vascular structure.

In the linear structure extraction device according to still another aspect of the present disclosure, the linear structure may be a center line along a route of a trachea, and a class classified by the third processing module may include a specific anatomical name in a tracheal structure.

In the linear structure extraction device according to still another aspect of the present disclosure, the third processing module may be configured by a neural network, and the third processing module may include a region-of-interest pooling layer that cuts out a local image of the anchor including the element point predicted by the second processing module from the feature map and deforms the local image to a fixed size, and at least one of a convolutional layer or a fully bonded layer to which the local image deformed into the fixed size is input.

Still another aspect of the present disclosure relates to a linear structure extraction method that extracts element points which constitute a linear structure from an image, the method comprising by using a learning model that is learned to receive an input of the image and output, as a prediction result, one or more element points which constitute the linear structure from the image, receiving the input of the image to the learning model, generating a feature map representing a feature amount of the image by performing convolution processing on the input image by using a first processing module, and dividing the feature map into a plurality of units including regions having a predetermined size in a grid pattern and calculating, for each unit, a shift amount from a unit center point to the element point of the linear structure closest to the unit center point by using a second processing module.

The linear structure extraction method according to still another aspect of the present disclosure may further comprise deleting, from a point cloud of a plurality of the element points predicted by the plurality of units, a part of excess element points close to each other by less than a first interval, which is half of the size of the unit as a standard, and selecting and leaving the element points at a degree of the first interval.

In the linear structure extraction method according to still another aspect of the present disclosure, the linear structure may be a representative line of a region having a thickness in the image, and the linear structure extraction method may further comprise deleting, from a point cloud of a plurality of the element points predicted by the plurality of units, a part of excess element points close to each other by less than a second interval, which is half of the thickness as a standard, and selecting and leaving the element points at a degree of the second interval.

The linear structure extraction method according to still another aspect of the present disclosure may further comprise deleting, from a point cloud of a plurality of the element points predicted by the plurality of units, an isolation point around which other points are not present within a distance of a predetermined threshold value.

Still another aspect of the present disclosure relates to a program that causes a computer to realize a function of extracting element points which constitute a linear structure from an image, the program causing the computer to realize a function of receiving an input of the image, a function of performing convolution processing on the input image by using a first processing module and generating a feature map representing a feature amount of the image, and a function of dividing the feature map into a plurality of units including regions having a predetermined size in a grid pattern and predicting, for each unit, a shift amount from a unit center point to the element point of the linear structure closest to the unit center point by using a second processing module.

Still another aspect of the present disclosure relates to a learned model that is learned to output, as a prediction result, one or more element points which constitute a linear structure from an input image, the model comprising a first processing module that receives the image and generates a feature map representing a feature amount of the image by convolution processing, and a second processing module that calculates a shift amount from a unit center point to the element point of the linear structure closest to the unit center point, for each unit obtained by dividing the feature map into a plurality of the units including regions having a predetermined size in a grid pattern.

In the learned model according to still another aspect of the present disclosure, parameters of networks which configure the first processing module and the second processing module may be decided by executing the machine learning by using a plurality of pieces of learning data in which a training image and positional information of the linear structure included in the training image are combined.

In the learned model according to still another aspect of the present disclosure, the linear structure may be a representative line of a region having a thickness in the image, and the learning data further may include thickness information of the region having the thickness included in the training image.

Still another aspect of the present disclosure relates to a linear structure extraction device comprising a processor, and a non-temporary computer-readable medium that stores a command for causing the processor to execute processing of extracting element points which constitute a linear structure from an image, in which the processor executes the command to perform processing including receiving the input of the image, generating a feature map representing a feature amount of the image by performing convolution processing on the input image by using a first processing module, and dividing the feature map into a plurality of units including regions having a predetermined size in a grid pattern and calculating, for each unit, a shift amount from a unit center point to the element point of the linear structure closest to the unit center point by using a second processing module.

According to the present invention, it is possible to predict the element points of the linear structure included in the image by using the learning model, and can detect the linear structure by the point cloud of the element points. According to the present invention, it is possible to easily reconstruct the linear structure from the point cloud of the predicted element points. For learning the learning model, a coordinate of the point on the line of the linear structure of a correct to the training image need only be used, and it is relatively easy to create such correct data.

DESCRIPTION OF THE PREFERRED EMBODIMENTS

A preferred embodiment of the present invention will be described below in detail with reference to the accompanying drawings.

Example of Detection of Tubular Structure In Medical Image

An example of a case in which a tubular structure is detected from a medical image will be described as an embodiment of the present invention. In recent years, with the progress of a medical device such as a multi-slice computed tomography (CT) device, a high-quality three-dimensional image is used for an image diagnosis. However, the three-dimensional image is configured by a large number of slice images and has a large amount of information, so that in some cases, it may take time for a doctor to find and diagnose a desired observation site.

Therefore, by extracting an organ of interest from the three-dimensional image and performing a display such as maximum intensity projection (MIP), volume rendering (VR), or curved planer reconstruction (CPR), the visibility of the entire organ and/or a lesion is enhanced, and the efficiency of the diagnosis is improved. For example, in a case in which analysis with respect to a cardiac CT image, particularly analysis with respect to a coronary artery or analysis with respect to a cerebral blood vessel is performed, it is required to extract a blood vessel route from the image.

Figure 1:
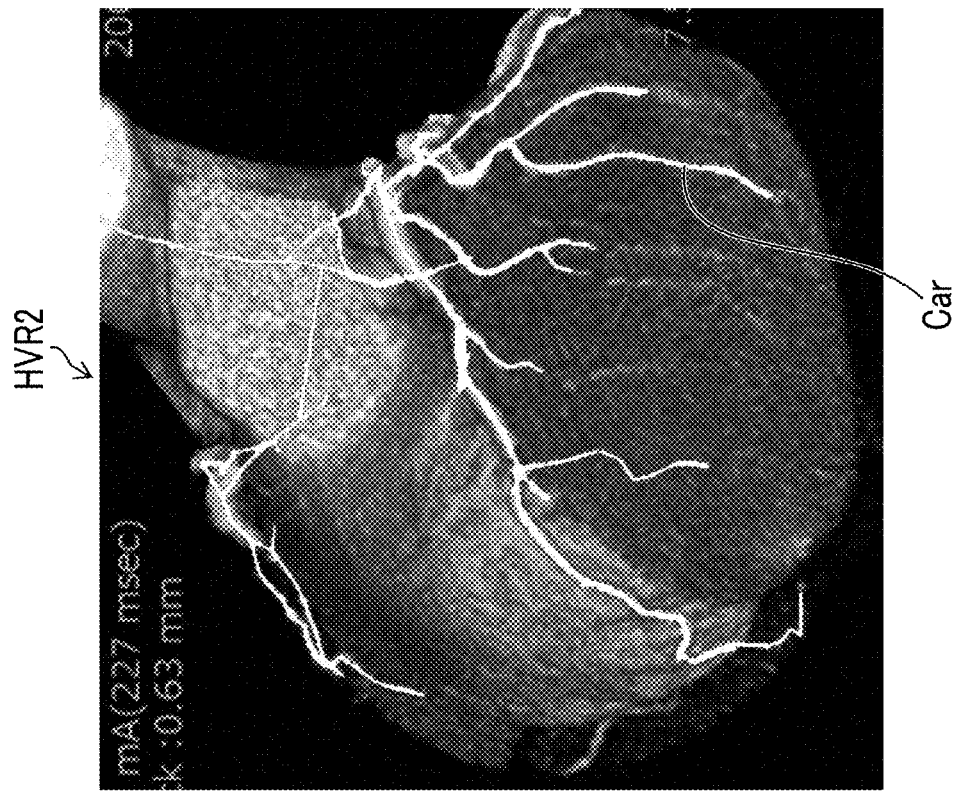
FIG. 1 is an example of a volume rendering (VR) image obtained by a cardiac CT examination.
Figure 1:
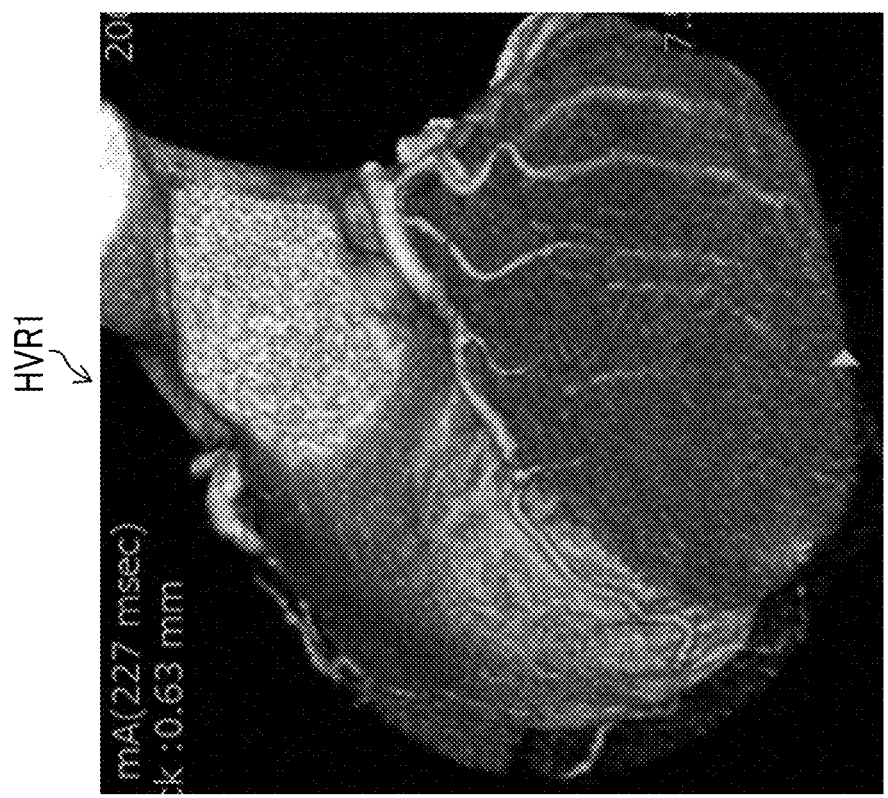

FIG. 1 is an example of a VR image obtained by a cardiac CT examination. An image HVR1 shown on the left side of FIG. 1 is an example of a cardiac VR image, and an image HVR2 shown on the right side is an example of the cardiac VR image in which a coronary artery route Car is superimposed and displayed.

Figure 2:
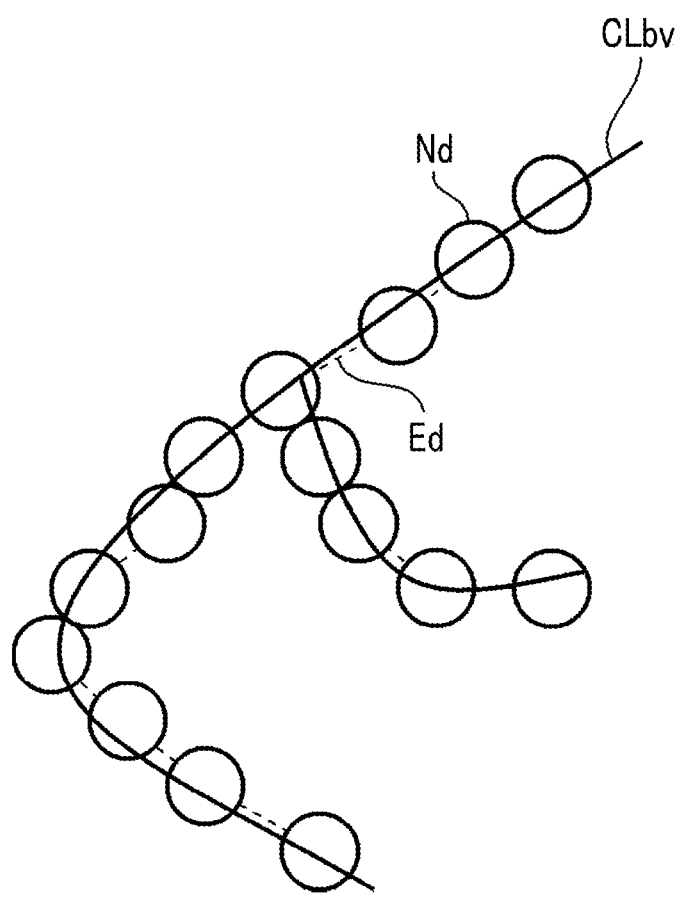
FIG. 2 is a schematic diagram of a blood vessel route represented by using a node and an edge.

FIG. 2 is a schematic diagram of the blood vessel route. The blood vessel route can be represented by using a point cloud of coordinate points (node Nd) that continuously trace a center line CLbv of the blood vessel and an edge Eg representing an adjacency relationship between the nodes Nd. In a case in which the center line CLbv of the blood vessel is detected from the three-dimensional image, the plaque accumulated in the blood vessel can be visualized and a stenosis rate can be measured by generating a CPR image developed along the route, so that information useful for the diagnosis can be obtained.

Figure 3:
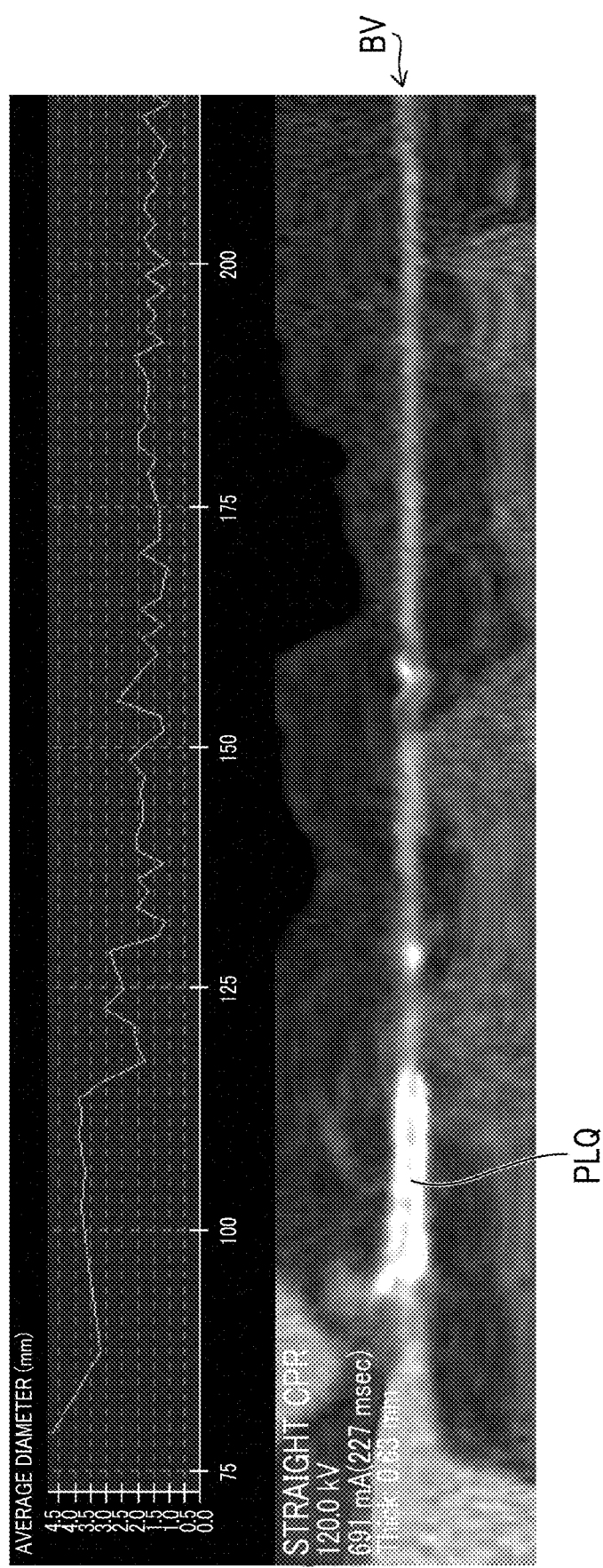
FIG. 3 is an example of a curved planer reconstruction (CPR) image of a coronary artery.

FIG. 3 is an example of the CPR image of the coronary artery. An example of the CPR image in a straight view mode is shown in the lower part of FIG. 3, and a graph of an average diameter for each position along a route of a blood vessel BV is displayed in the upper part of FIG. 3. In the CPR image shown in FIG. 3, a portion in which a part of the blood vessel BV is swollen in white is plaque PLQ.

Outline of Linear Structure Extraction Device

A linear structure extraction device according to the embodiment of the present invention is applied to processing of extracting a center line of a tubular structure applied to support the image diagnosis as described with reference to FIGS. 1 to 3. Here, as a specific application example, it is assumed that a structure of a portal vein and a vein of a liver is detected from an abdomen three-dimensional CT image. The blood vessel is an example of a "tubular structure" in the present disclosure, and the center line of the blood vessels is an example of a "linear structure" in the present disclosure. The linear structure extraction device according to the present embodiment predicts (estimates) a collection of points which constitute the center line of the blood vessels from an input image, that is, a plurality of the points on the center line, and performs labeling of the classification of each point. A point cloud on the center line may be paraphrased as a "point sequence".

The linear structure extraction device according to the present embodiment improves a framework of a Faster R-CNN, which is an object detection algorithm, and performs processing of predicting the points on the line, which constitute the linear structure from the image. That is, the object, which is a detection target, in the present embodiment is the center line of the blood vessels, and an output as a prediction result (estimation result) is positional information of the points that are the elements which constitute the center line, that is, the points on the center line. The points that are the elements which constitute the linear structure are referred to as "element points of the linear structure". Hereinafter, the element points of the center line are referred to as the "points on the center line".

In the present specification, the term "object" is not limited to a physically existing "substance", and includes, for example, the concept of a representative line of a region, such as a crack and a gap, or a region having a size, the linear structure, and the element points of the linear structure. The center line of the blood vessels is an example of the representative line of the tubular structure having the thickness. Since the description of the processing by using the three-dimensional image is complicated, hereinafter, the description will be made by replacing with a case in which the input image is a two-dimensional image in order to facilitate understanding.

[Outline of Faster R-CNN]

Figure 4:
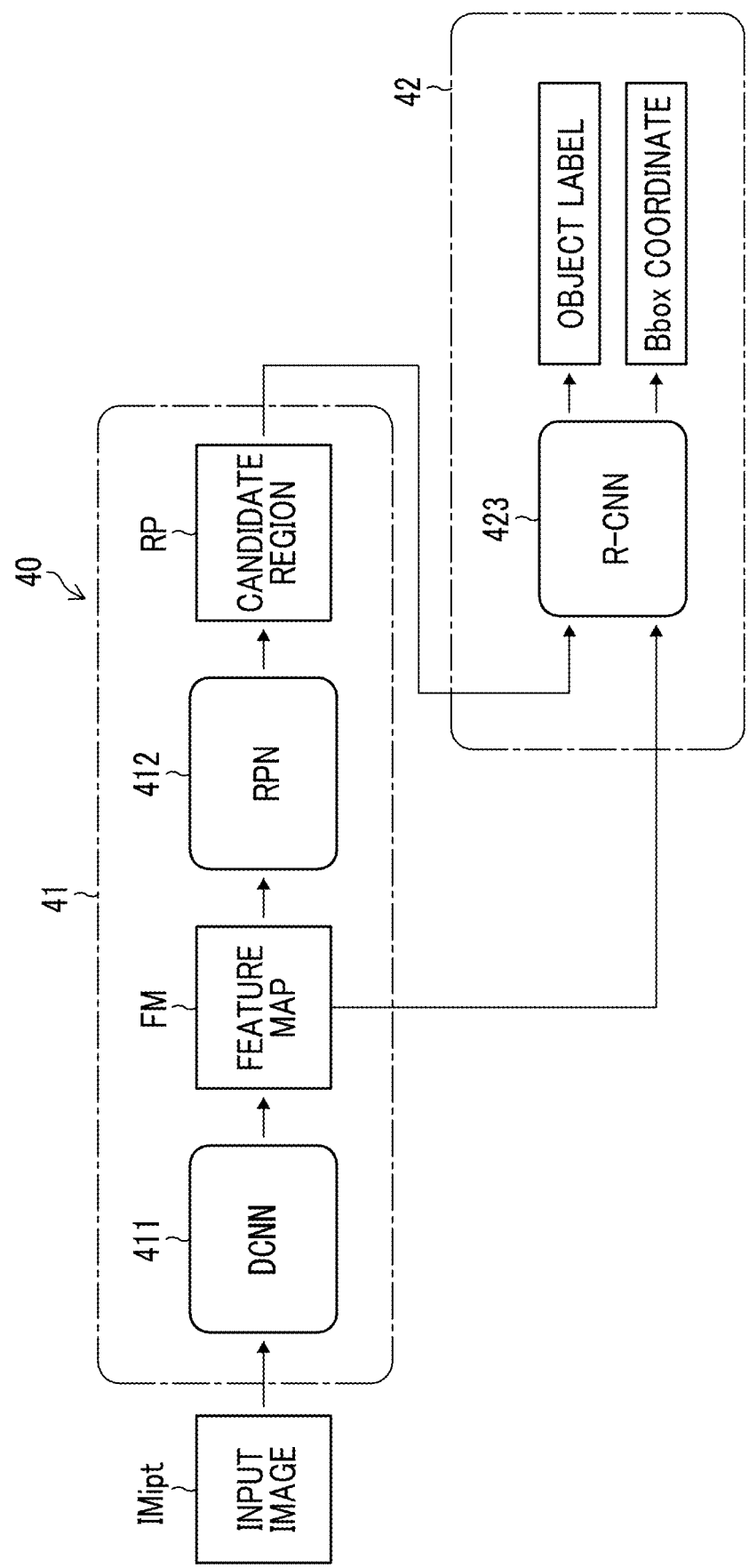
FIG. 4 is a configuration diagram showing an outline of a Faster R-CNN, which is applied to an embodiment of the present invention.

FIG. 4 is a configuration diagram showing an outline of the Faster R-CNN, which is applied to the embodiment of the present invention. A Faster R-CNN 40 is configured to include a first neural network 41 that finds a region in which the object is likely to be present from the image of an input image IMipt, and a second neural network 42 that performs classification processing of specifying what the object in a candidate region RP, for each candidate region RP obtained as an output of the first neural network 41.

The first neural network 41 is configured to include a deep convolutional neural network (DCNN) 411 and a region proposal network (RPN) 412. The DCNN 411 is a neural network that extracts a feature amount of the input image IMipt. A size of a filter and the number of channels used for convolution of the DCNN 411 can be appropriately designed. For example, the filter may be a 3×3 filter, and the number of channels in a hidden layer may be 256, 512, or the like.

In a case in which the input image IMipt is input to the DCNN 411, a feature map FM is output from the DCNN 411. The feature map FM is a convolution feature map obtained by multi-layer convolution operation. The DCNN 411 may include a pooling layer, or may reduce the size of the feature map FM by setting the stride of the convolution filter to 2 or the like without providing the pooling layer. The feature map FM output from DCNN 411 is input to the RPN 412.

The RPN 412 uses the feature map FM output from the DCNN 411 as an input, and predicts the candidate region RP, which seems to be the object, from the feature map FM. The RPN 412 is configured to include a convolutional layer, and generates a bounding box (Bbox) including a thing, which seems to be the object, from the image. A list of the candidate regions RP predicted by the RPN 412 is transmitted to the second neural network 42. That is, the RPN 412 lists a plurality of the candidate regions RP from the image and transmits the listed candidate regions RP to an R-CNN 423.

The second neural network 42 is configured by the region-based convolutional neural network (R-CNN) 423. The R-CNN 423 performs the classification with respect to each candidate region RP obtained as the output of the RPN 412. In addition to the task of the classification, the R-CNN 423 may output the bounding box that represents a rectangle surrounding the object. Note that the term rectangle is not limited to a rectangle having a long side and a short side, but also includes a square.

The R-CNN 423 is connected to the DCNN 411, and the feature map FM, which is output from the DCNN 411, is input to the R-CNN 423. Further, data of the candidate region RP predicted by the RPN 412 is input to the R-CNN 423. The R-CNN 423 projects the candidate region RP generated by RPN 412 onto the feature map FM, cuts out a region of interest (ROI), which is an operation target, performs the classification of the object for each ROI, and decides a label. The R-CNN 423 performs the classification with respect to each candidate region RP obtained as the output of the RPN 412.

Further, the R-CNN 423 may output the bounding box that surrounds the detected object. In the task of the object detection by using, as a target, a subject captured in a general photographic image disclosed in U.S. Pat. No. 9,858,496B and Ren, Shaoqing, et al. "Faster R-CNN: Towards real-time object detection with region proposal networks." Advances in neural information processing systems. 2015, an output of an object label and an output of the bounding box that represents a bounding rectangle of the object are obtained from the R-CNN 423.

In a case of the present embodiment, it is considered that even in a case in which the rectangle that surrounds the "points on the center line", which is the element points of the linear structure is output, it is poor in practice use, and thus the output of the bounding box may be omitted. Alternatively, if necessary, the bounding box including the points on the center line and a region range at a degree of a thickness of the blood vessel around the center line may be output.

[Contents of Processing in Linear Structure Extraction Device]

Figure 5:
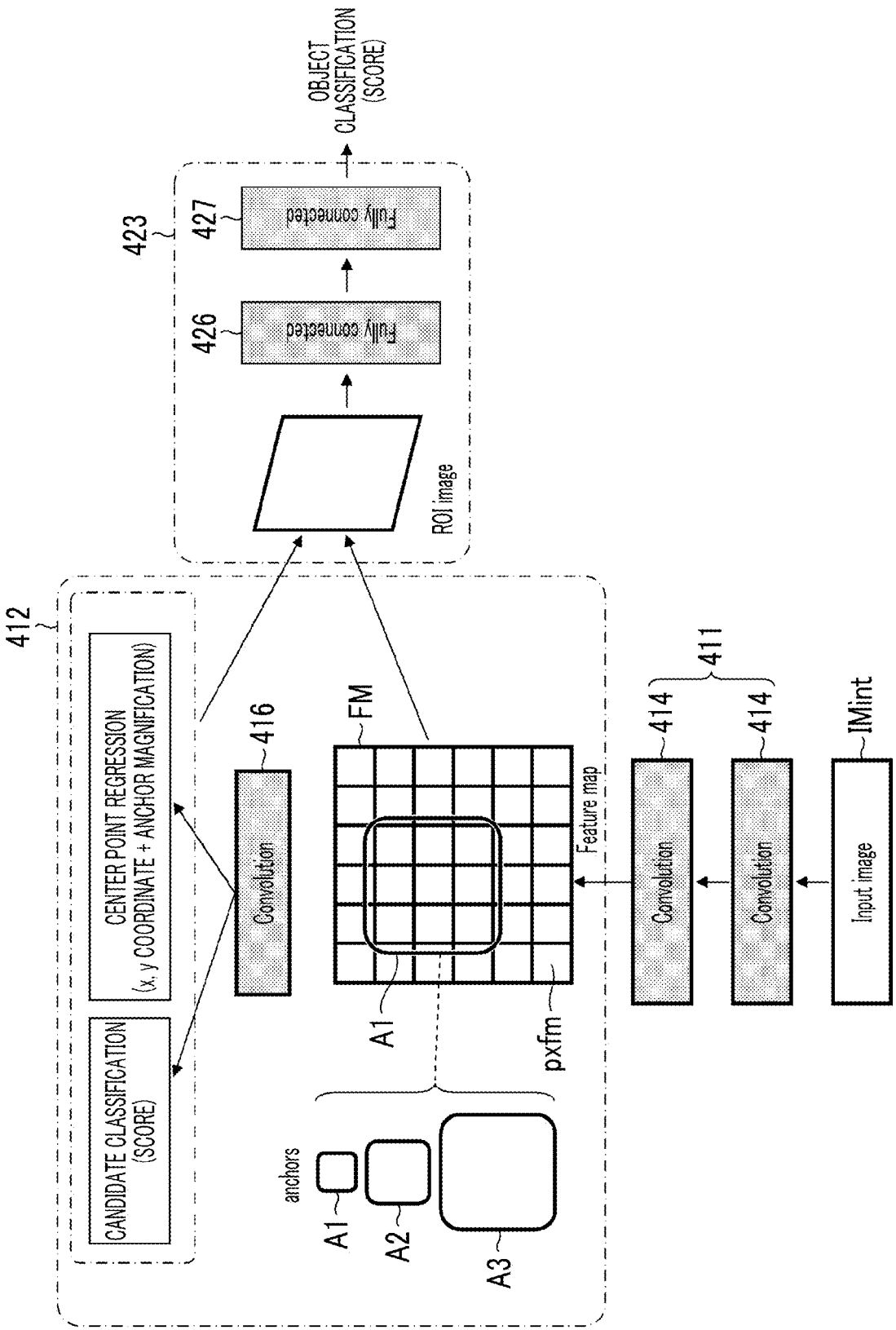
FIG. 5 is an explanatory diagram schematically showing contents of processing by a linear structure extraction device according to the embodiment of the present invention.

FIG. 5 is an explanatory diagram schematically showing contents of processing in a linear structure extraction device 50 according to the embodiment of the present invention. In FIG. 5, the elements common to those in FIG. 4 are designated by the same reference numerals. The linear structure extraction device 50 can be realized by a calculation system (computing system) configured by using one or a plurality of computers. The linear structure extraction device 50 comprises the DCNN 411 as a first processing module, the RPN 412 as a second processing module, and the R-CNN 423 as a third processing module. The term "module" includes the concept of a program module.

The DCNN 411 receives the input image IMipt, performs convolution processing by a plurality of convolutional layers 414, and generates the feature map FM. A leading input layer of the DCNN 411 has a role of an image reception unit that receives the input image IMipt. 6×6 grid shown in FIG. 5 represents a part of the feature map FM, and one compartment of a square of the grid corresponds to a pixel pxfm of the feature map FM. One pixel pxfm of the feature map FM has information on the feature amount calculated from a wide-range image region in the input image IMipt.

In a case in which the pixel of the input image IMipt is expressed as a pixel px, the DCNN 411 is configured in which one pixel pxfm of the feature map FM has the feature amount calculated from a pixel region having an S×S pixel size in a grid array of the pixels px of the input image IMipt. S is a value in accordance with a reduction rate of the image by the DCNN 411. That is, it is understood that each pixel pxfm of the feature map FM corresponds to the pixel region having the S×S size at the corresponding position in the input image IMipt.

Stated another way, each region having the S×S size in a case in which the input image IMipt is divided into a plurality of regions having the S×S size in a grid pattern corresponds to the pixel pxfm of the feature map FM. The position of each pixel pxfm of the feature map FM can be described by projecting the position thereof onto a coordinate system that represents an image position in the input image IMipt.

The RPN 412 receives the feature map FM output from the DCNN 411, and predicts the point on the center line closest to a center point of the pixel pxfm, for each pixel pxfm of the feature map FM. The point on the center line closest to the center point of the pixel pxfm is referred to as a "closest point". Each pixel pxfm of the feature map FM is a unit of a region for predicting a shift amount to the closest point, and is referred to as a "unit". That is, the feature map FM is divided into a plurality of the units (pixels pxfm) having a predetermined size region in a grid pattern, and the RPN 412 predicts the closest point, which is a candidate for the element point of the center line, for each unit of the feature map FM.

The RPN 412 applies a plurality of reference rectangles having different aspect ratios and/or sizes to each unit of the feature map FM in order to predict the closest point for each unit of the feature map FM. The reference rectangle is referred to as an "anchor". FIG. 5 shows an example in which three types of the anchors having different sizes, an anchor A1, an anchor A2, and an anchor A3 are used. Here, the aspect ratios of all three types of the anchors are 1:1. Note that a plurality of the anchors having the same size and different aspect ratios may be used. A plurality of the anchor A1, the anchor A2, and the anchor A3 are disposed such that each of the center points thereof coincides with the center point of the unit (pixel pxfm).

The RPN 412 has a convolutional layer 416 that calculates how much each anchor is moved (shifted) and/or deformed to approach a correct rectangle, and calculates whether or not there is the object in the anchor. The correct rectangle here is a rectangle having the point on the correct center line at the center position, the rectangle having a region size in accordance with the thickness of the blood vessel. The RPN 412 comprises the convolutional layer different from the DCNN 411. For example, the RPN 412 may have a configuration providing a smaller number of convolutional layers than the DCNN 411. The RPN 412 performs the convolution processing, for each unit, by using the feature amount of the unit position.

The RPN 412 performs, through the convolution by the convolutional layer 416, an output of the shift amount of the anchor center point and a deformation amount of the anchor for allowing the anchor to approach the correct rectangle, and an output of a score representing the certainty of two-classification indicating whether or not there is the object in the anchor. That is, the RPN 412 solves, for each anchor, "a regression problem of how the anchor is moved and/or deformed to coincide with ground truth" and "an identification problem of whether or not there is the object in the anchor". Note that the deformation amount of the anchor may be, for example, the deformation magnification in each direction of an x direction and a y direction. In a case in which similar deformation that corrects only the size without changing the aspect ratio of the anchor is performed, the deformation amount of the anchor may be the deformation magnification common to the x direction and the y direction.

The score of the two-classification indicating whether or not there is the object in the anchor is called an "objectness score". On the other hand, regression result data showing the shift amount and the deformation amount of the anchor to allow the anchor to approach the correct rectangle is collectively referred to as "Bbox offset". The RPN 412 may calculate the objectness score indicating whether or not there is the object in the anchor shifted by the calculated shift amount, may calculate the objectness score indicating whether or not there is the object in the anchor which is not shifted (in the anchor disposed at the unit position), or may calculate both the objectness scores.

The R-CNN 423 generates a local image obtained by cutting out a portion corresponding to the candidate region from the feature map FM based on the candidate region of the prediction result output from the RPN 412, calculates the score of the classification of the object included in an ROI image by fully bonded layers 426 and 427 based on the ROI image, which is the cut out local image, and provides a class label based on the score. Note that the size of the local image cut out from the feature map FM may be different from the size of the candidate region.

Hereinafter, the RPN 412 and the R-CNN 423 will be described in more detail.

[Description of RPN 412]

For example, the RPN 412, which is used for extraction of the blood vessel in the liver, is trained to present a candidate point on the center line of the blood vessels, regardless of the portal vein or the vein. Each pixel of the feature map obtained from a final layer of RPN 412 is a unit that predicts the candidate point on the center line. Each unit corresponds to the pixel pxfm of the feature map FM described with reference to FIG. 5. Each unit predicts a deviation amount from the position of the closest point of the center line with respect to the center position of the unit.

In the case of the two-dimensional image, the deviation amount predicted by the RPN 412 is two real values $\Delta x$ and $\Delta y$ indicating the deviation amount in each of the x direction and the y direction. In the case of the three-dimensional image, the deviation amount predicted by the RPN 412 is three real values $\Delta x$, $\Delta y$, and $\Delta z$ indicating the deviation amount in each of the x direction, the y direction, and the z direction. Further, the RPN 412 simultaneously determines whether or not there is a target object in the anchor shifted in accordance with the predicted deviation amount and/or in the anchor which is not shifted. That is, the RPN 412 performs the two-classification indicating whether or not there is the target object.

Figure 6:
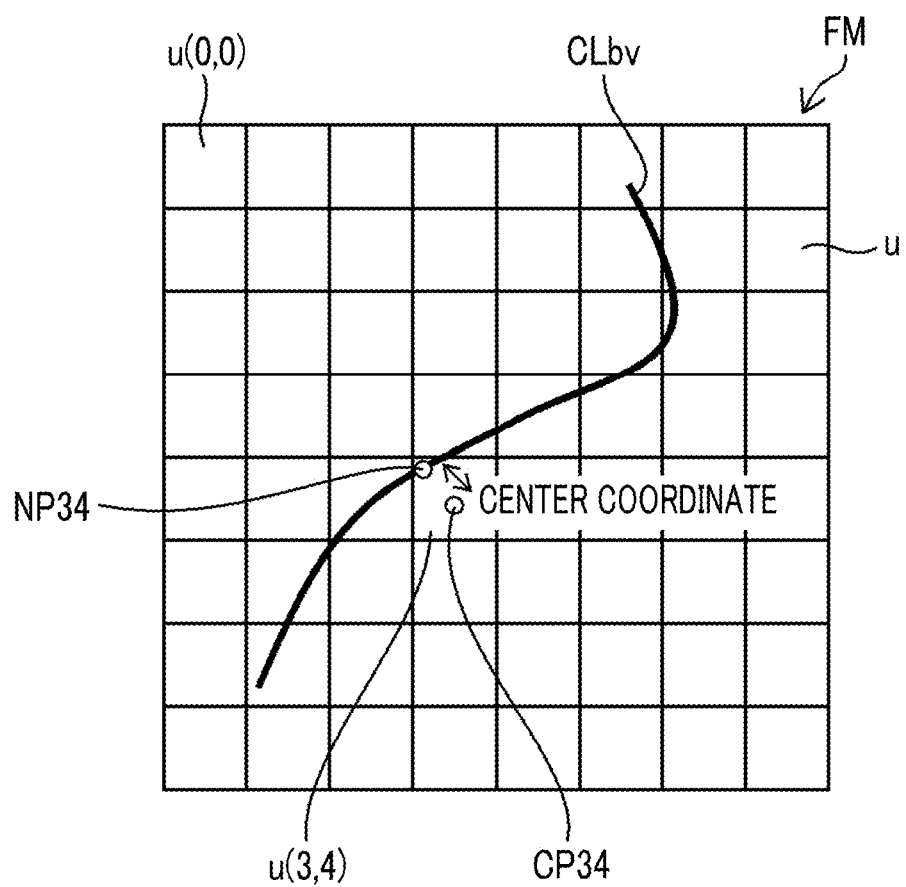
FIG. 6 is a diagram schematically showing an example of a positional relationship between each pixel of a feature map processed by a region proposal network (RPN) and a blood vessel center line.

FIG. 6 is a diagram schematically showing an example of a positional relationship between each pixel of the feature map processed by the RPN 412 and a blood vessel center line. 8×8 grids shown in FIG. 6 represent a part of the feature map FM from the DCNN 411. For example, in FIG. 6, in a case in which a position of each unit u is expressed as "u(column number, row number)" by using column numbers 0 to 7 and row numbers 0 to 7 of the grid, the upper left unit is expressed as u(0, 0), the lower right unit is expressed as u(7, 7). For example, the unit u(3, 4) predicts a deviation amount ($\Delta x$, $\Delta y$) between a center coordinate CP34 of the unit center position and a position of a closest point NP34 of the center line CLbv closest to the center coordinate CP34.

Note that a space that defines the coordinate may be an xy coordinate system that specifies the position in the input image IMipt. That is, the center coordinate and the closest point coordinate of each unit are represented by numerical values (x, y) in the xy coordinate system that specify the position in the image of the input image IMipt. Similarly for the other units, the deviation amount ($\Delta x$, $\Delta y$) from the position of the closest point of the center line CLbv is predicted with reference to the center coordinate of each unit. The center coordinate of the unit u is an example of a "unit center point" in the present disclosure. The predicted "deviation amount" is an example of a "shift amount" from the unit center point to the closest point in the present disclosure.

Figure 7:
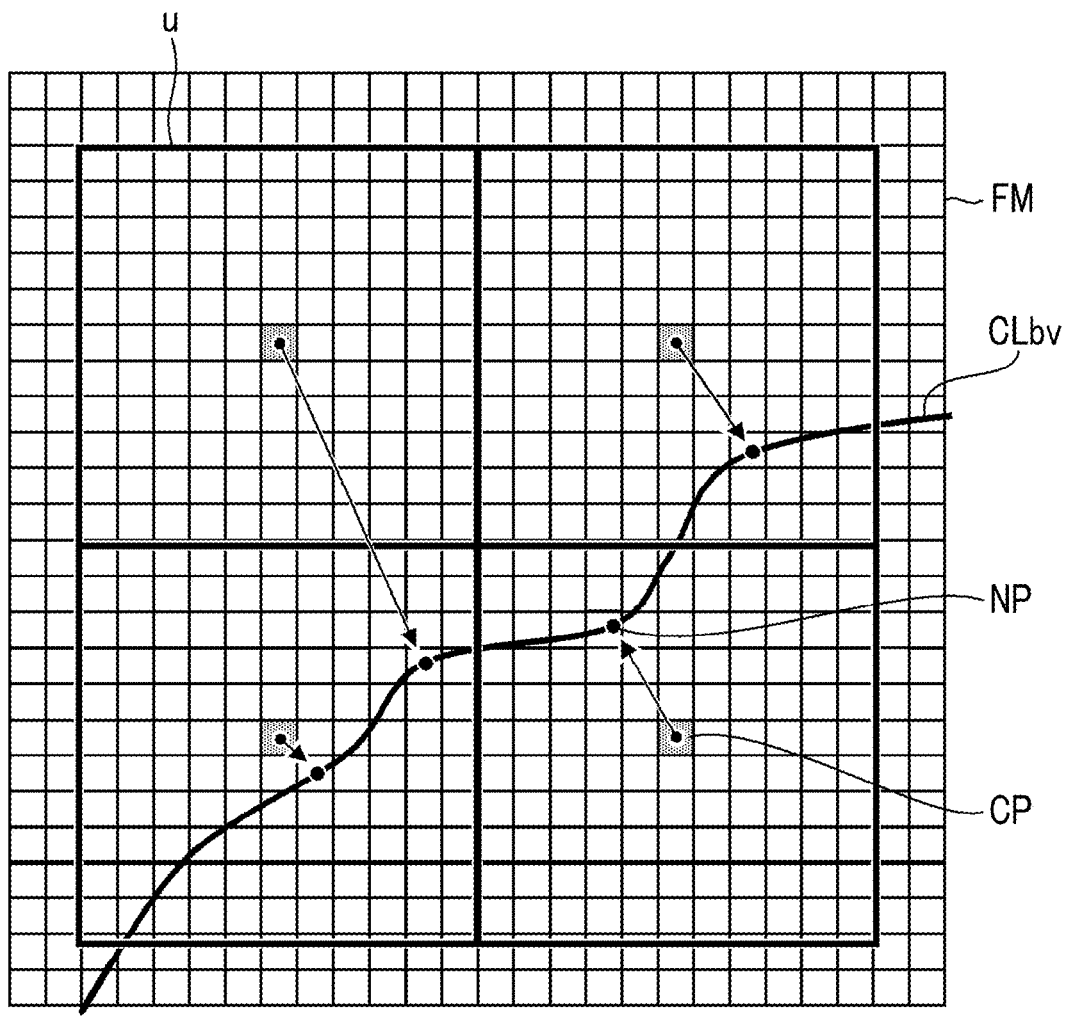
FIG. 7 is an enlarged diagram of a unit in a vicinity of a center line CLbv.

FIG. 7 is an enlarged diagram of a unit of the center line CLbv. Here, four of the units u are shown. The square of the fine grid displayed in the unit u schematically represents a pixel size of the input image IMipt. A closest point NP of the center line CLbv is predicted from a center coordinate CP of each unit u as shown in FIG. 7.

<Description of Anchor>

Figure 8:
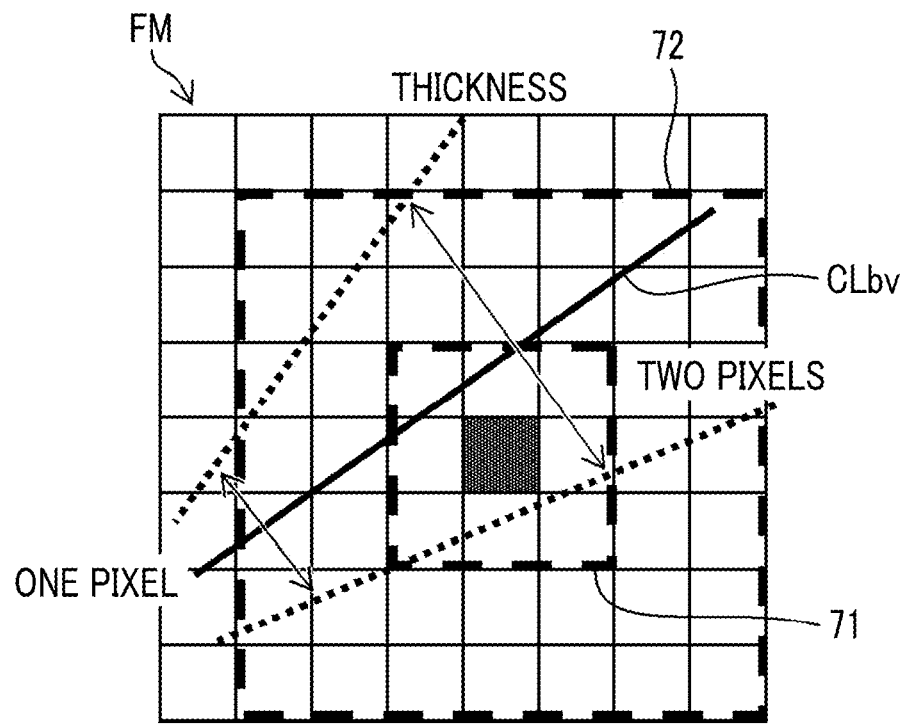
FIG. 8 is an explanatory diagram of an anchor.

FIG. 8 is an explanatory diagram of the anchor. FIG. 8 shows a part of the feature map FM as in FIG. 6, and the grid square represents the pixel of the feature map FM, that is, the unit. Each unit imaginarily has a plurality of predefined anchors. FIG. 7 shows two types of the anchors for simplifying the description. FIG. 7 shows a first anchor 71 and a second anchor 72 disposed in the unit u(4, 4) filled with gray. The first anchor 71 is an anchor having a pixel size of 3×3. The second anchor 72 is an anchor having a pixel size of 7×7.

It is assumed that the thickness of the blood vessel is defined in accordance with the position on the center line CLbv of the blood vessel. Among the plurality of anchors disposed in each unit, only the anchor having the size which most approaches a target thickness predicts the position of the point on the center line.

A plurality of types of the anchors are prepared such that a range of the target thickness is covered. For example, in a case in which the coronary artery is a target, three-sized square anchors with sides of 3 pixels, 5 pixels, and 9 pixels are prepared. Note that in a case in which the object detection is performed with a general object as a target disclosed in Ren, Shaoqing, et al. "Faster R-CNN: Towards real-time object detection with region proposal networks." Advances in neural information processing systems. 2015, the plurality of anchors having different aspect ratios are prepared, but in a case of the present embodiment, the detection target is the tubular structure having the linear structure extending in various directions, there is no particular tendency for directionality such as vertical or horizontal, and thus the aspect ratio of the anchor may be only 1:1.

In a case of FIG. 8, a vicinity of the lower left of the center line CLbv, for example, a vicinity of the unit u(1, 5) has the thickness of the blood vessel of approximately 1 pixel in radius. On the other hand, a vicinity of the unit u(4, 3) positioned near the upper right of the center line CLbv has the thickness of the blood vessel of approximately 2 pixels in radius. Therefore, in the unit disposed in the lower left portion of FIG. 8, among the plurality of anchors, the anchor having a pixel size of 3×3 is used for the prediction of the position of the point on the center line, and in the unit disposed in the upper right portion of FIG. 8, the anchor having a pixel size of 7×7 is used for the prediction of the position of the point on the center line.

Figure 9:
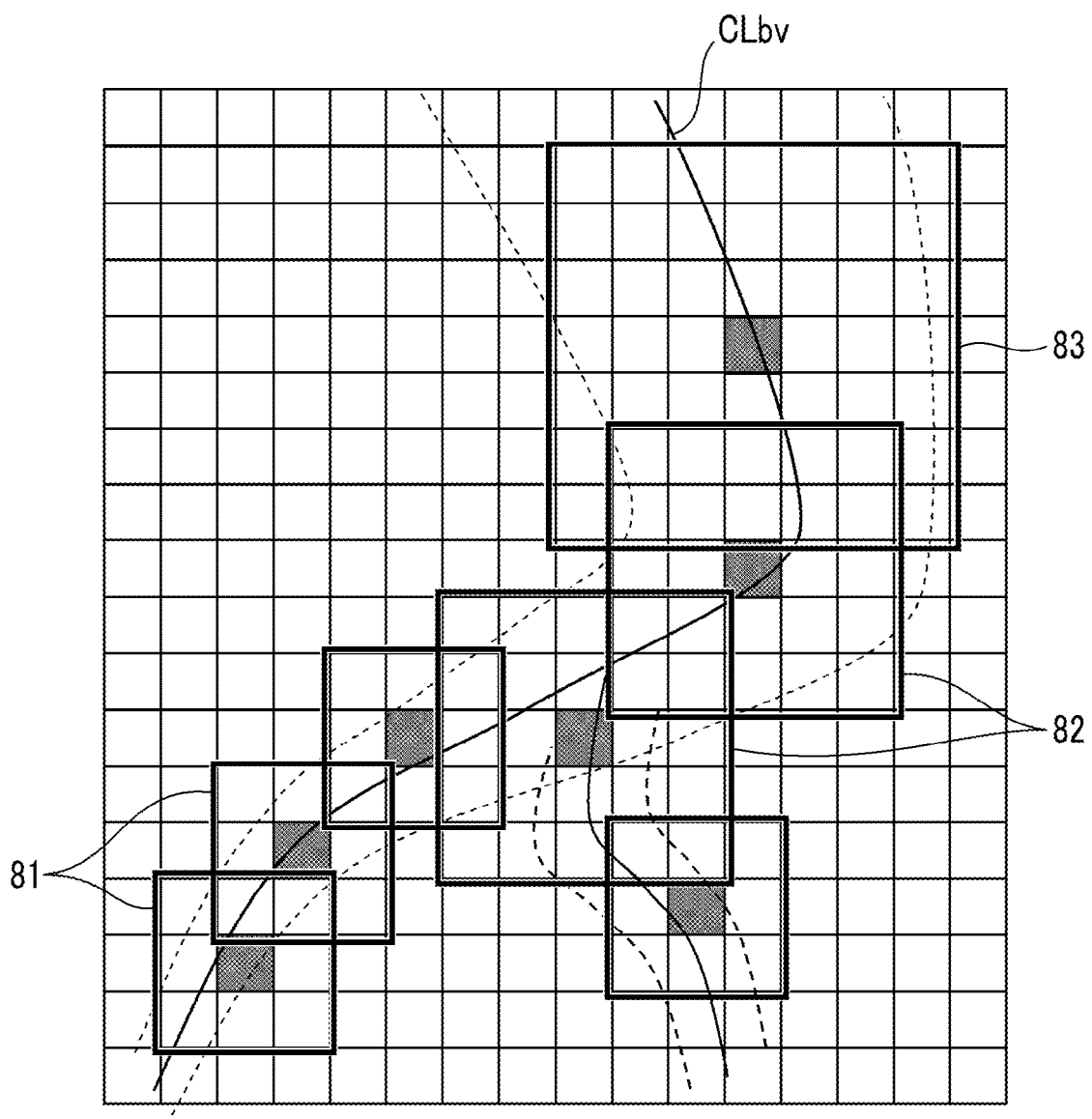
FIG. 9 is a diagram showing an example in which three types of the anchors having different sizes are used.

FIG. 9 shows an example in which three types of the anchors having different sizes are used, and shows that the anchor used for the prediction of the point on the center line is decided in accordance with the thickness of the blood vessel. In this example, an anchor 81 having a side of 3 pixels, an anchor 82 having a side of 5 pixels, and an anchor 83 having a side of 7 pixels are prepared, and the size of the anchor to be applied is changed in accordance with the thickness of the blood vessel. Note that it is not necessary to limit the number of the anchors used for the prediction for one unit to one, and depending on the thickness of the blood vessel, the plurality of anchors may be applied to one unit to predict the point on the center line.

As the learning data used for learning, the positional information of the correct center line is provided to the training image, and information indicating what size of a region (here, the thickness of the blood vessel) each point on the correct center line represents is provided. That is, as the learning data, information (score) indicating that each point on the correct center line is to be extracted by the anchor of what size, that is, is to be extracted as a representative point of what thickness is provided. As a result, it is possible to learn to change the size of the anchor in accordance with the thickness of the blood vessel of the region, which is a target.

Figure 10:
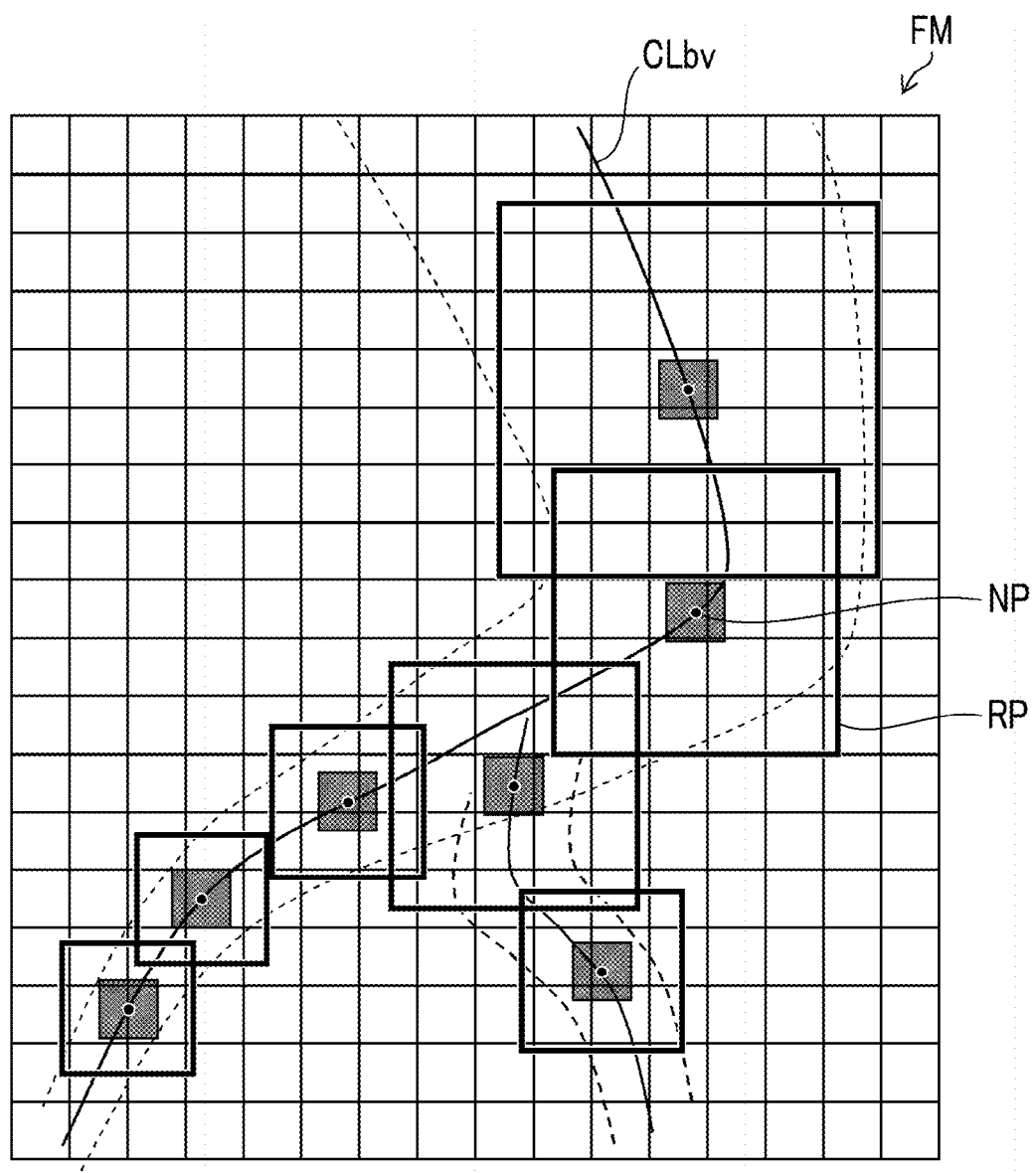
FIG. 10 is a conceptual diagram showing an output example of the RPN.

FIG. 10 is a conceptual diagram showing an output example of the RPN 412. FIG. 10 shows an example of the candidate regions RP obtained by performing, for each anchor, shift of the center point coordinate to the predicted closest point NP and rectangular size correction by the predicted deformation magnification shown in FIG. 9.

<Outline of Learning Method By Using Anchor>

An example of a procedure of a learning method by using the anchor is described below.

[Step 1] The RPN 412 disposes the plurality of predefined anchors in each unit (pixel) of the feature map FM output from the DCNN 411 by an input of the training image.

[Step 2] The RPN 412 searches for the anchor having a large overlap with the correct rectangle from among the plurality of anchors.

[Step 3] A difference between a selection anchor selected in step 2 and the correct rectangle is calculated. This difference may be, specifically, the shift amounts $\Delta x$ and $\Delta y$ of the anchor center coordinate and the deformation magnification for changing the size of the anchor.

[Step 4] The network is learned such that the objectness score of the selection anchor is "1" and a correction amount of the bounding box (Bbox offset) is the difference calculated in step 3.

<Outline of Inference Method By Using Anchor>

An example of an inference (prediction) method by using the anchor is described below.

[Step 101] The learned RPN 412 disposes the plurality of predefined anchors in each unit of the feature map FM output from the DCNN 411 by an input of an unknown image, which is an inference target.

[Step 102] The RPN 412 calculates the Bbox offset of each anchor and the objectness score.

[Step 103] For the anchor having a high objectness score, the anchor is moved and deformed based on the Bbox offset of the anchor.

<Suppression of Overlapping Candidate Regions: Non-Maximum Suppression (NMS) Processing>

In some cases, the point cloud of the points on the center line predicted by each unit is excessively large. As disclosed in U.S. Pat. No. 9,858,496B and Ren, Shaoqing, et al. "Faster R-CNN: Towards real-time object detection with region proposal networks." Advances in neural information processing systems. 2015, in the Faster R-CNN, NMS processing of selecting and leaving only an important candidate is inserted between the RPN and the R-CNN. The NMS processing is processing of leaving one rectangle among a plurality of rectangles indicating the same object and suppressing an output from another rectangle.

In cases of U.S. Pat. No. 9,858,496B and Ren, Shaoqing, et al. "Faster R-CNN: Towards real-time object detection with region proposal networks." Advances in neural information processing systems. 2015, the RPN calculates an intersection over union (IoU) value between the generated candidate regions, and in a case in which the IoU value is larger than a predetermined threshold value, it is considered that the overlap between the regions is large, and one region is deleted (suppressed). On the contrary, in a case in which the IoU value is small, the overlap between the regions is small, and thus both candidate regions are left as it is. A mechanism of reducing the number of excessively overlapping candidate regions is proposed by such an algorithm.

In a case of a problem of detection of the point cloud on the center line, which is a target in the present embodiment, it is sufficient that the "points on the center line" are detected at intervals of a degree of half of the thickness of the blood vessel. Therefore, in the present embodiment, in addition to the NMS processing described above or instead of the NMS processing, the IoU value described above is not calculated, and processing of thinning out the candidate regions is performed at intervals of a degree of half of the thickness of the blood vessel. Note that in a case in which the information on the thickness of the blood vessel is not provided in advance as teaching data in a case of learning, sampling need only be performed at a degree of pixel intervals of the unit.

<Removal of Isolation Point>

Figure 11:
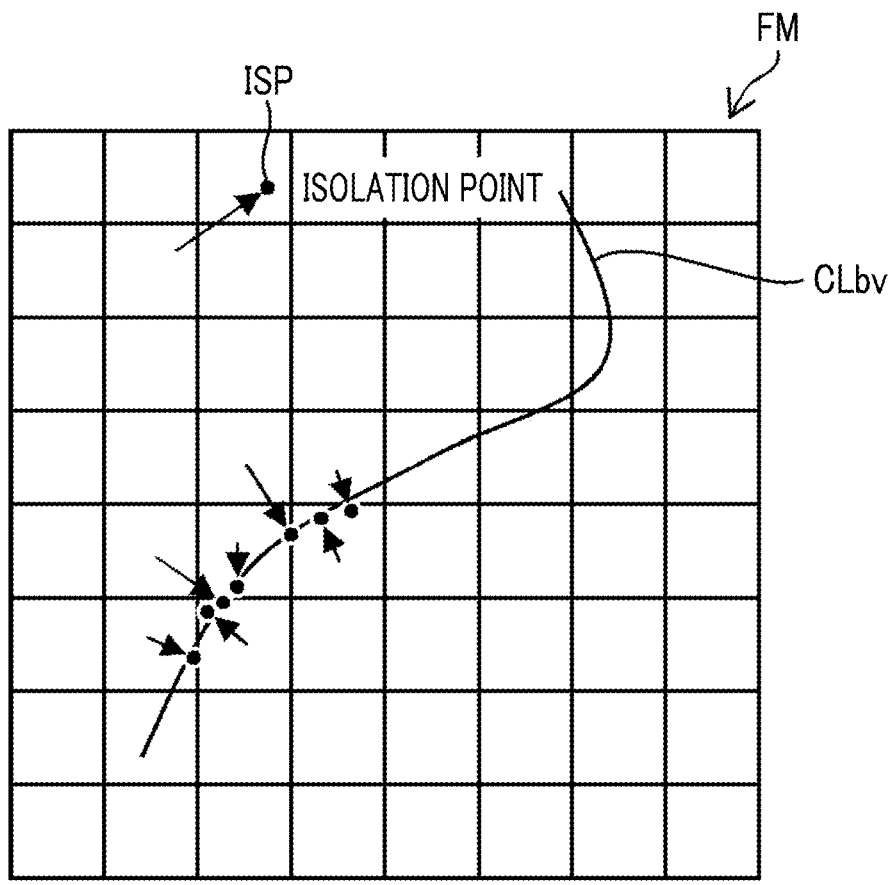
FIG. 11 is an explanatory diagram of an isolation point.

FIG. 11 shows an example of the candidate point predicted by the RPN 412, and is an explanatory diagram in a case in which the isolation point is included in the candidate point. Since the linear structure such as the center line of the blood vessels is represented by the array of continuous points (point sequence), as shown in FIG. 11, in a case in which the point on the center line predicted from each unit is present at a large distance from the other point sequences and is isolated, there is a high possibility that an isolation point ISP is a falsely predicted result (false detection). Therefore, in the RPN 412, in a case in which the predicted candidate point on the center line is isolated, a predetermined threshold value that can be determined as the false detection is set, and in a case of a point around which other candidate points are not present in a distance within the threshold value, the isolation point ISP thereof is deleted (removed) from the prediction result.

[Description of R-CNN 423]

The R-CNN 423 performs the classification by using, as an input, the image obtained by standardizing the feature map in the anchor predicted by the RPN 412. In a case in which the detection target is a tree structure of graph theory, such as a vascular structure handled in the present embodiment, the R-CNN 423 performs the classification into any one of four labels as a "root", a "point on a twig", a "branch point", or a "peripheral point (tip)" as constituting elements of the tree structure.

Figure 12:
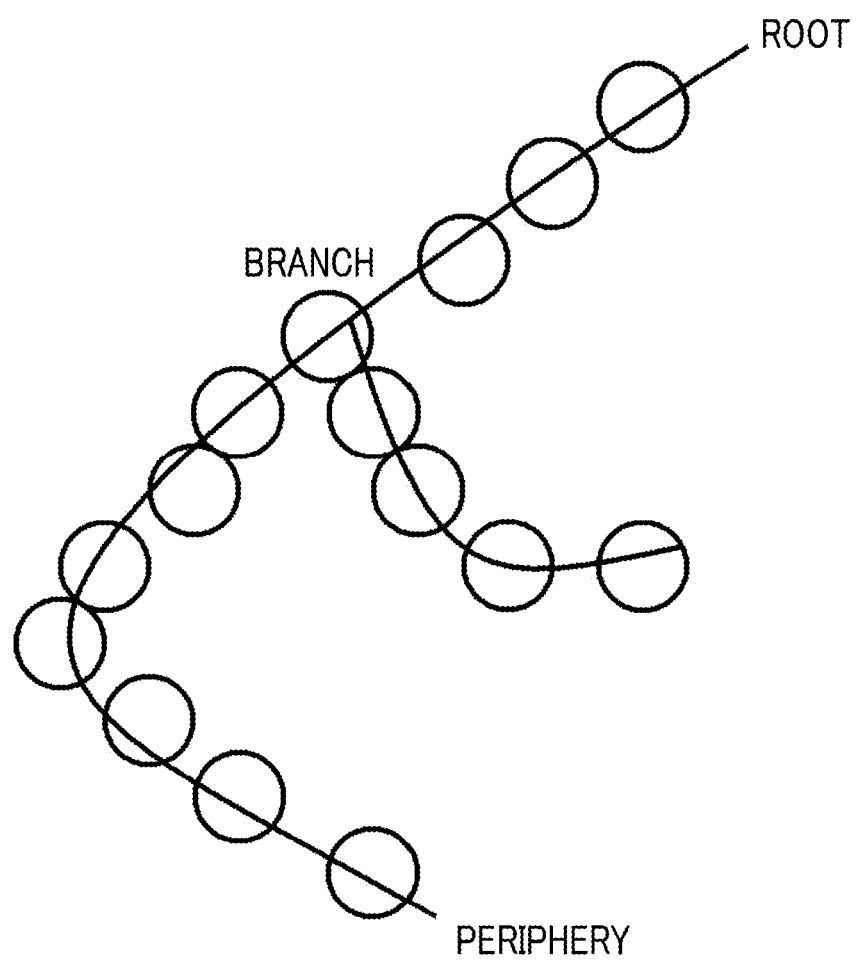
FIG. 12 shows an example of a point cloud provided with labels of constituting elements of a tree structure.

FIG. 12 shows an example of the point cloud provided with the labels of the constituting elements of the tree structure. In a case in which a characteristic (classification) of each point is known in advance in this way, it is convenient to connect the points in the subsequent stage to reconstruct a graph structure. For example, a search for the route can be started from a position of the root, the number of twigs can be increased at the branch point, and the route connection can be terminated at the peripheral point.

The existing algorithm, such as a minimum spanning tree algorithm or a shortest route (Dijkstra) algorithm, can be used for the route connection.

Other Examples of Classification

There are various vascular systems in a human body, such as a liver or lungs. The vascular system of the liver includes an artery, the portal vein, and the vein. The respective vascular systems are in contact with each other or intersect each other, and it is important to separate the target in order to understand the anatomy. Therefore, a configuration may be adopted in which the R-CNN 423 performs the classification of the types of the blood vessels. In this case, an anatomical name need only be provided as an item of a class to be classified, and the data of the label, which is the correct, need only be added to the learning data.

[Case of Liver]

For the purpose of classification of the blood vessels in the liver, the classes classified by the R-CNN 423 for the candidate points (points on the predicted center line) detected by the RPN 412 are set to four classes of {the portal vein, the vein, the artery, and others}, depending on the types of the blood vessels.

Further, the liver is anatomically divided into eight areas. The eight areas are caudate lobe, a lateral dorsal area, a lateral caudal area, a medial area, an anterior rostral area, an anterior caudal area, a posterior occipital area, and a posterior caudal area. Since these areas are defined by running of vascular twigs, eight types of the vascular twigs can be classified.

For the provided correct center line, the anatomical name is provided to each twig. The label of the candidate point on the predicted center line is used as the correct label learned by the R-CNN 423.

In the human body, in addition to the liver, there is a tree structure (called "graph" in a broad sense in a case in which a loop is present), such as cerebral blood vessels, pulmonary blood vessels, bronchi, or gastrointestinal tract. A method in the present disclosure can be applied to the recognition of various anatomical structures.

[Case of Lungs]

In a case of the pulmonary vascular structure, for example, a pulmonary vein and a pulmonary artery can be classified. Alternatively, for the tracheal structure having tracheal and bronchial tree structures, a plurality of classifications can be performed by an anatomical bronchial name and/or an area name. The lungs are divided into a plurality of areas by bronchial twigs. For example, the classification can be made into classes of the trachea, the main bronchus of the right lung, the upper lobe bronchus, the apical bronchus (B1), the posterior bronchus (B2), the anterior bronchus (B3), the truncus intermedius, the middle lobe bronchus, the lateral bronchus (B4), the medial bronchus (B5), the lower lobe bronchus, the superior bronchus (B6), the medial basal bronchus (B7), the anterior basal bronchus (B8), the lateral basal bronchus (B9), the posterior basal bronchus (B10), the basal bronchus, the main bronchus of the left lung, the upper lobe bronchus, upper segment bronchus, the apical posterior bronchus (B1+2), the anterior bronchus (B3), the ramus lingularis, the ramus lingularis superior (B4), the ramus lingularis inferior (B5), the lower lobe bronchus, the superior bronchus (B6), the medial anterior basal bronchus (B7+8), the lateral basal bronchus (B9), the posterior basal bronchus (B10), the basal bronchus, and the like.

Example of Learning Model Used In Linear Structure Extraction Device

Figure 13:
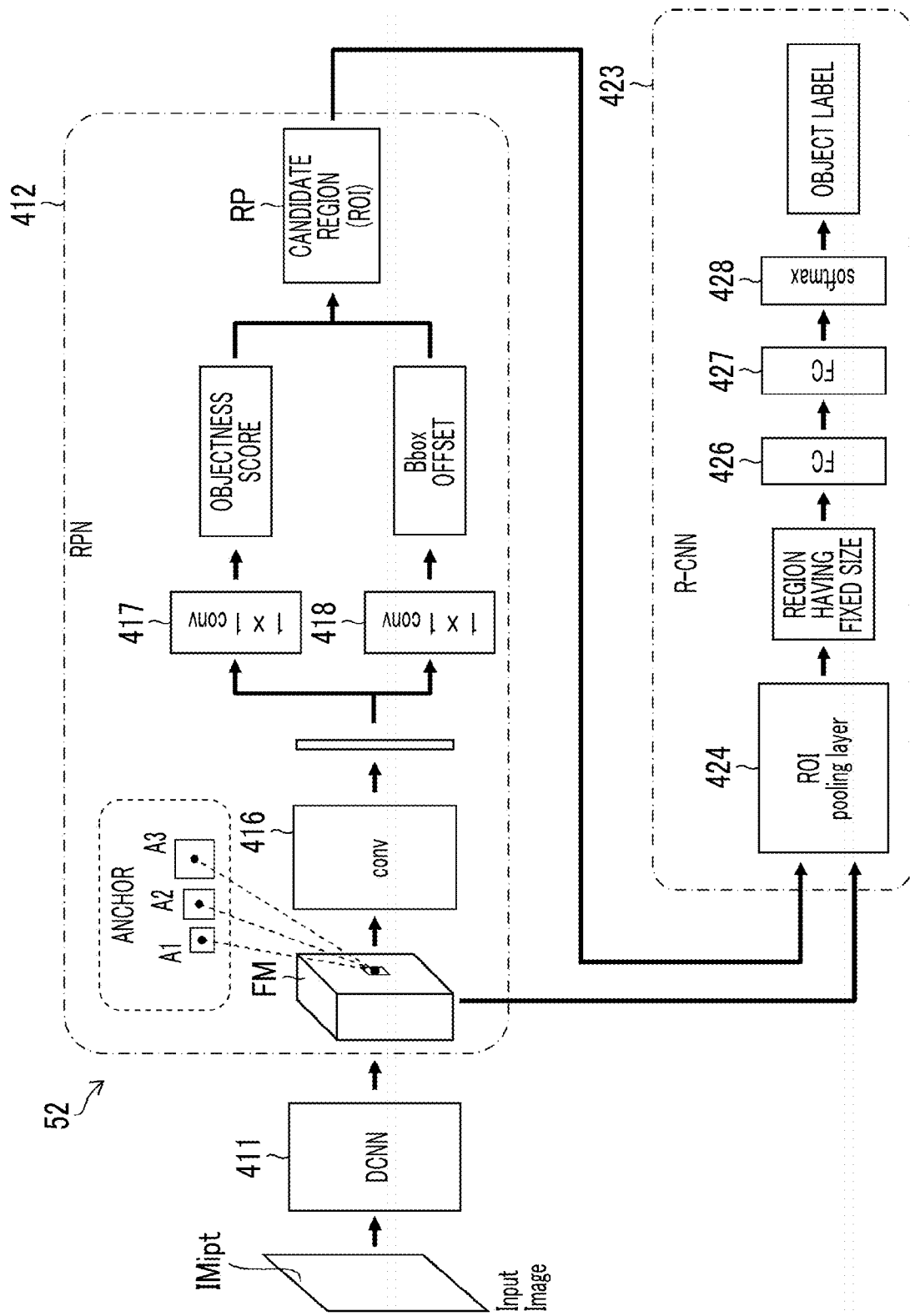
FIG. 13 is an explanatory diagram schematically showing a network structure of a learning model implemented on the linear structure extraction device, and a flow of processing.

FIG. 13 is an explanatory diagram schematically showing a network structure of a learning model 52 implemented on the linear structure extraction device 50, and a flow of processing. The elements corresponding to the elements described in FIGS. 4 and 5 are designated by the same reference numerals in FIG. 13, and the description thereof will be omitted. The learning model 52 includes the DCNN 411, the RPN 412, and the R-CNN 423.

The convolutional layer 416 of the RPN 412 has the number of filters in accordance with the number of channels of the feature map FM output by the DCNN 411. For example, the filter size of the convolutional layer 416 may be 3×3.

The RPN 412 has two types of 1×1 convolutional layers 417 and 418 in the subsequent stage of the convolutional layer 416. An output of the convolutional layer 416 is input to each of the 1×1 convolutional layers 417 and 418. The 1×1 convolutional layer 417 includes a softmax layer that uses a softmax function as an activation function, and outputs the objectness score indicating a probability of being the object (point on the center line) at each anchor position. The 1×1 convolutional layer 418 is a regression layer that performs numerical regression to allow the anchor to approach the correct rectangle for each of the plurality of anchors. The RPN 412 is trained such that the overlap with the correct rectangle of the training data is large.

The R-CNN 423 includes an ROI pooling layer 424, fully bonded layers 426 and 427, and a softmax layer 428. The ROI pooling layer 424 pools the feature map in the region corresponding to each candidate region RP cut out from the feature map FM obtained from the DCNN 411, and deforms the pooled feature map into a standardized image having a fixed size. A partial image of the feature map deformed into the fixed size is input to the fully bonded layer 426. The softmax layer 428 is provided in the subsequent stage of the final fully bonded layer 427. The number of units in an output layer is decided in accordance with the number of classes to be classified, the object score indicating the probability of being each class is calculated, and finally the object label is specified. Note that a configuration may be adopted in which the convolutional layer is provided in place of or in addition to a part or all of the fully bonded layers 426 and 427.

The ROI pooling layer 424 shown in FIG. 13 is an example of a "region-of-interest pooling layer" in the present disclosure. The learning model 52 is an example of a "learned model" in the present disclosure.

<Linear Structure Extraction Method According to Present Embodiment>

Figure 14:
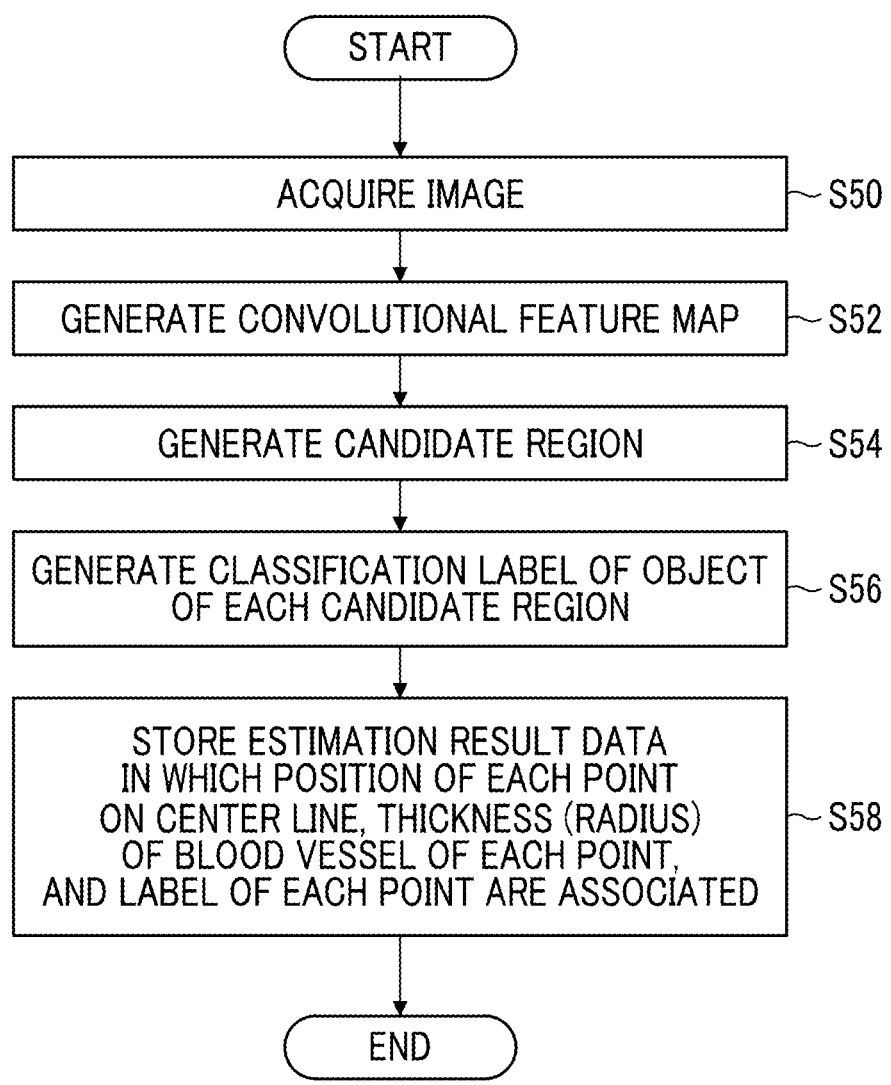
FIG. 14 is a flowchart showing an example of the contents of the processing by the linear structure extraction device.

FIG. 14 is a flowchart showing an example of the contents of the processing by the linear structure extraction device 50. The processing shown in FIG. 14 is executed by the calculation system that functions as the linear structure extraction device 50. The calculation system executes the processing of each step in accordance with a program stored on a computer-readable medium.

In step S50, the calculation system receives the image, which is a processing target.

In step S52, the calculation system generates the convolution feature map by the DCNN 411 from the input image.

In step S54, the calculation system inputs the convolution feature map, which is output from the DCNN 411, to the RPN 412, and generates the candidate region that seems to be the point on the center line by the RPN 412.

In step S56, the calculation system inputs the information on each candidate region generated by the RPN 412 and the convolution feature map generated by the DCNN 411 to the R-CNN 423, cuts out each candidate region by the R-CNN 423, and generates a classification label of the object of each candidate region.

In step S58, the calculation system stores the data of the prediction result in which the position of each point on the center line predicted by the RPN 412, the thickness of the blood vessel of each point, and the label of each point predicted by the R-CNN 423 are associated.

After step S58, the calculation system terminates the flowchart of FIG. 14.

Figure 15:
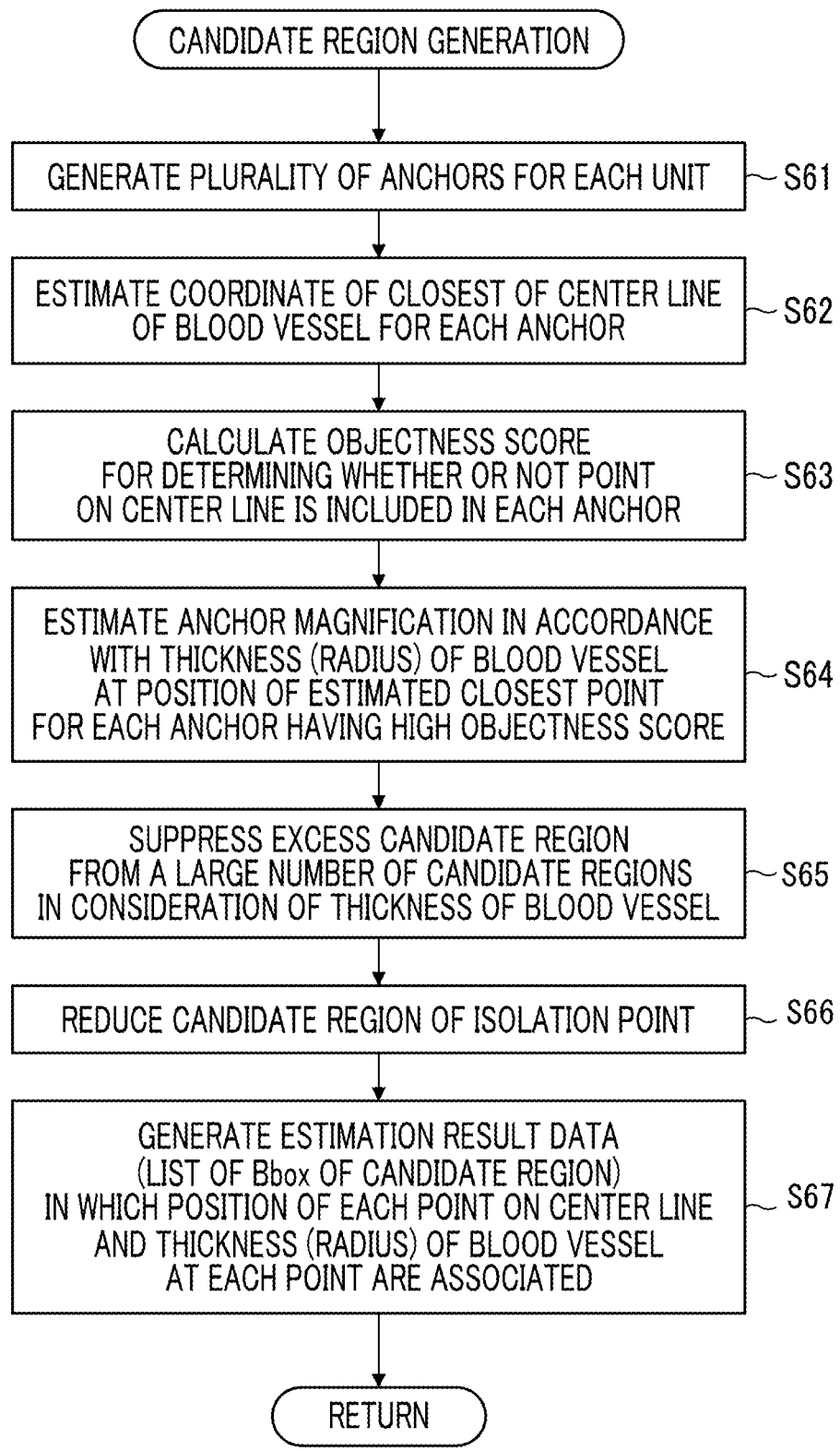
FIG. 15 is a flowchart showing an example of the contents of the processing applied to step S54 of FIG. 14.

FIG. 15 is a flowchart showing an example of the contents of the processing applied to step S54 of FIG. 14. In step S61 of FIG. 15, the calculation system generates the plurality of anchors for each unit of the convolution feature map.

In step S62, the calculation system predicts, for each anchor, the coordinate of the point (closest point) on the center line of the blood vessels, which is closest to the anchor center point.

In step S63, the calculation system calculates the objectness score for the two-classification indicating whether or not the center line point is included in each anchor.

In step S64, the calculation system predicts, for the anchor having a high objectness score, the anchor magnification in accordance with the thickness of the blood vessel at the position of the predicted closest point.

In step S65, the calculation system suppresses the excess candidate region from a large number of candidate regions generated by the RPN 412 in consideration of the thickness of the blood vessel. For example, sampling is performed such that in the point cloud of a plurality of the candidate points predicted by the RPN 412, a part of excess candidate points close to each other by less than an interval (first interval), which is a degree of half of a diameter of the blood vessel (radius) as a standard, is deleted, and the candidate points at the interval of a degree of the radius of the blood vessel are selected and left. By such thinning sampling, the point sequence of the candidate points remains at a larger interval as the thickness of the blood vessel is thicker, and the candidate points remain at a smaller interval as the thickness of the blood vessel is thinner.

Note that in a case in which the information on the thickness of the detection target object is not provided in advance, sampling is performed such that in the point cloud of a plurality of the candidate points predicted by the RPN 412, a part of excess candidate points close to each other by less than an interval (second interval), which is a degree of half of a size of the unit u as a standard, is deleted, and the candidate points at the interval of a degree of half of the size of the unit u are selected and left.

In step S66, the calculation system determines the isolation point from the candidate point predicted by the RPN 412, and deletes the candidate region of the isolation point.

In step S67, the calculation system generates the data of the prediction result in which the position of each point on the predicted center line and the thickness of the blood vessel at each point are associated, that is, a list of the Bbox of the candidate region.

After step S67, the calculation system terminates the flowchart of FIG. 15, and returns to the flowchart of FIG. 14.

Example of Learning Method

Hereinafter, an example of the learning method of the learning model in the linear structure extraction device 50 according to the present embodiment will be described.

Example of Learning Data

As the learning data used for learning, a plurality of sets of the combination of the training image, the positional information of each point on the center line of the blood vessels included in the training image, the information on the thickness of the blood vessel at each point of the center line, and a correct label of the classification for each point are used. The "learning data" is data for training used for machine learning, and is synonymous with "data for learning" or "training data".

The training image may be, for example, a CT image captured by a CT device. As the positional information of each point on the provided correct center line of the blood vessels and the information on thickness of the blood vessel, for example, the coordinate of the point on the center line of the CPR image generated from the CT image and a numerical value of the blood vessel radius can be used.

By specifying the thickness of the blood vessel (radius) of each point, for example, it is possible to automatically determine the correct rectangle of the square with one side having a length twice the radius centered on the point. In addition, the size of the anchor suitable for the prediction of the point can be determined from the provided blood vessel thickness of each point. The correct label of the classification of each point can be determined based on anatomical findings. For one training image, the correct data of the position at which it is desire to extract the anchor of each size is provided for each type (size) of the anchor. Note that depending on the thickness of the blood vessel, the correct data may be provided such that duplicate predictions are performed by using the plurality of anchors of different sizes.

Figure 16:
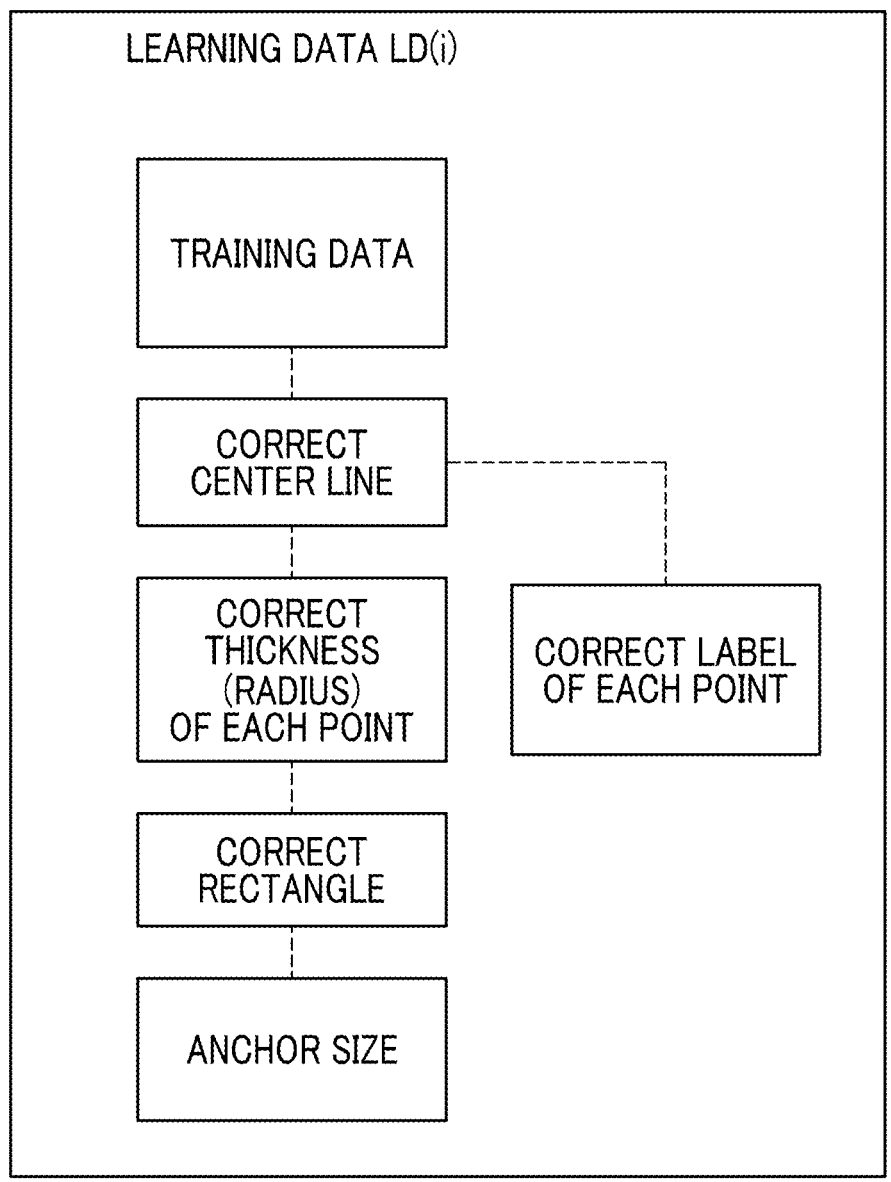
FIG. 16 is a conceptual diagram of the learning data.

FIG. 16 is a conceptual diagram of learning data LD(i). In the machine learning of the present embodiment, the training image, the coordinate of each point of the correct center line, the correct thickness of each point, and the correct label of each point are provided as the learning data LD(i). i is an index number for identifying the learning data. Note that the coordinate of each point of the correct center line may be provided as a numerical value in sub-pixel units, which is finer than pixel units of the training image. The correct rectangle can be automatically generated from the information on the correct thickness. The size of the anchor may be automatically generated from the information on the correct thickness, or may be designated by an operator.

Configuration Example of Learning Device

Figure 17:
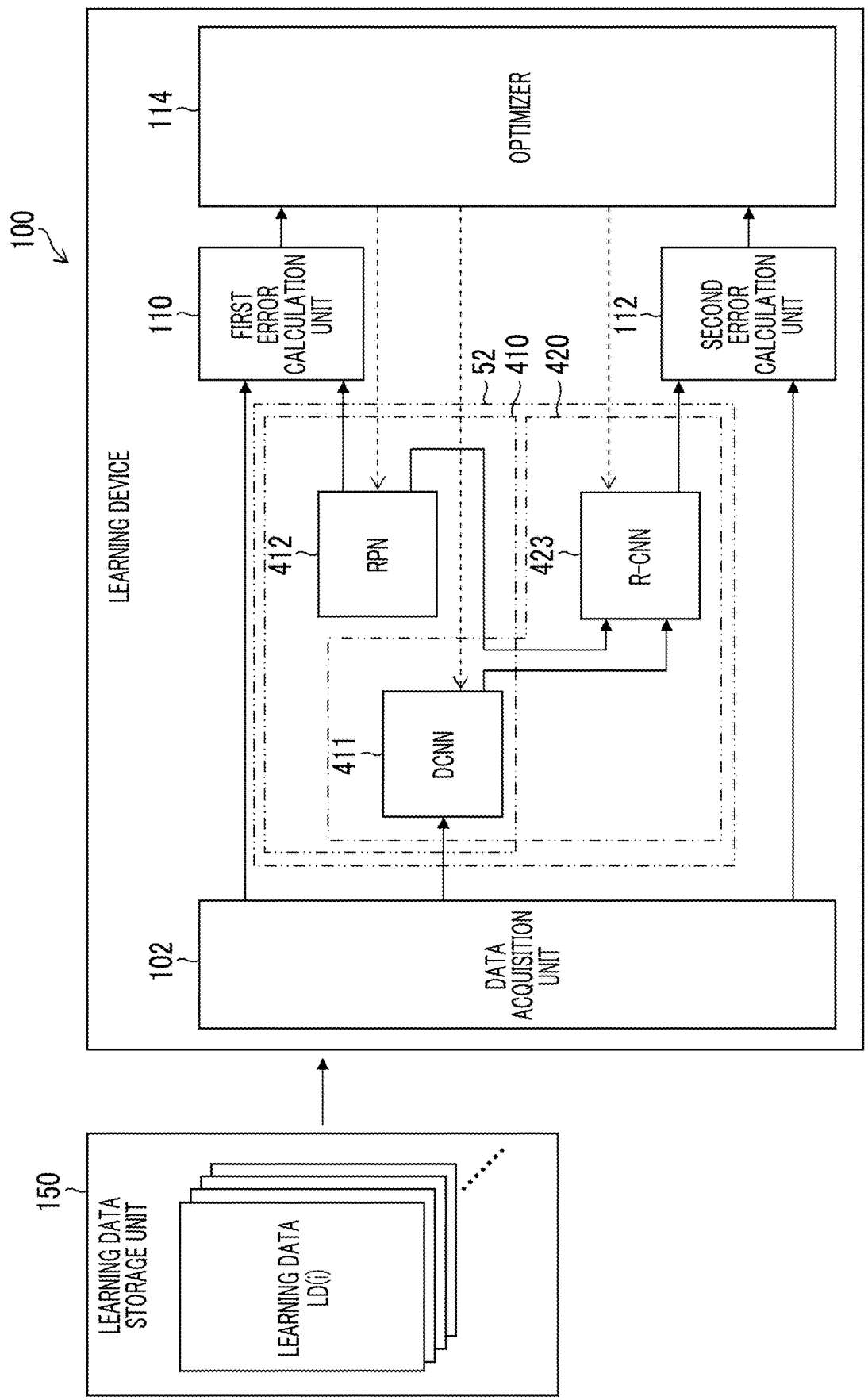
FIG. 17 is a functional block diagram showing a configuration example of a learning device which performs machine learning.

FIG. 17 is a functional block diagram showing a configuration example of a learning device 100 which performs the machine learning. The learning device 100 can be realized by the calculation system configured by using one or a plurality of computers. The calculation system which constitutes the learning device 100 may be the same system as the calculation system which constitutes the linear structure extraction device 50, a different system, or a system that shares a part of elements.

The learning device 100 is connected to a learning data storage unit 150. The learning data storage unit 150 is configured to include a storage that stores the learning data LD(i) necessary for the learning device 100 to perform the machine learning. Here, an example will be described in which the learning data storage unit 150 and the learning device 100 are respectively configured as separate devices, but these functions may be realized by one computer, or the processing functions may be allocated and realized by two or more of a plurality of computers.

For example, the learning data storage unit 150 and the learning device 100 may be connected to each other via an electric telecommunication line (not shown). The term "connection" is not limited to wired connection, and also includes the concept of wireless connection. The electric telecommunication line may be a local area network, or may be a wide area network.

With this configuration, the generation processing of the learning data and the learning processing of the learning model can be performed without being physically and temporally restricted by each other.

The learning device 100 reads the learning data LD(i) from the learning data storage unit 150 and executes the machine learning. The learning device 100 can perform reading of the learning data LD(i) and updating of the parameters in units of mini-batch in which a plurality of pieces of the learning data LD(i) are collected.

The learning device 100 includes a data acquisition unit 102, a learning model 52, a first error calculation unit 110, a second error calculation unit 112, and an optimizer 114.

The data acquisition unit 102 is an interface that introduces the learning data LD(i). The data acquisition unit 102 may be configured by a data input terminal that introduces the learning data LD(i) from other signal processing units outside or inside the device. Further, the data acquisition unit 102 may employ a wired or wireless communication interface unit, may employ a media interface unit that performs reading and writing of a portable external storage medium such as a memory card, or may employ an appropriate combination of these aspects.

As described above, the learning model 52 includes the DCNN 411, the RPN 412, and the R-CNN 423.

The first error calculation unit 110 calculates an error between the prediction result output from the RPN 412 and the correct data for each anchor. The first error calculation unit 110 evaluates the error by using a loss function. A first error calculated by the first error calculation unit 110 is transmitted to the optimizer 114.

The second error calculation unit 112 calculates the error between the prediction result output from the R-CNN 423 and the correct label. The second error calculation unit 112 evaluates the error by using the loss function. A second error calculated by the second error calculation unit 112 is transmitted to the optimizer 114.

The optimizer 114 performs processing of updating the parameters of the learning model 52 from calculation results of the first error calculation unit 110 and the second error calculation unit 112. The optimizer 114 performs updating of the parameters based on the algorithm such as a back propagation method. The network parameters include a filter coefficient (weight of connection between nodes) of filters used to processing each layer, node bias, and the like.

The optimizer 114 calculates an update amount of the parameter of a first subnetwork 410 obtained by connecting the DCNN 411 and the RPN 412 by using the calculation result of the first error calculation unit 110, and performs the parameter updating processing of updating the parameters of the network of at least the RPN 412 of the DCNN 411 and the RPN 412 in accordance with the calculated update amount of the parameter. Preferably, the parameters of the respective networks of the DCNN 411 and the RPN 412 are updated.

Further, the optimizer 114 calculates the update amount of the parameter of a second subnetwork 420 obtained by connecting the DCNN 411 and the R-CNN 423 by using the calculation result of the second error calculation unit 112, and updates the parameter of the network of each of the DCNN 411 and the R-CNN 423 in accordance with the calculated update amount of the parameter.

Further, the learning device 100 further performs learning for the model of the first subnetwork 410 in a state in which the parameter of the DCNN 411 finely tuned by the training of the second subnetwork 420 are fixed, and updates the parameter of the RPN 412. By repeatedly executing such a learning process, the parameters of the learning model 52 can be optimized. As described above, the learned learning model 52 can be obtained.

Example of Learning Method By Using Learning Device 100

Figure 18:
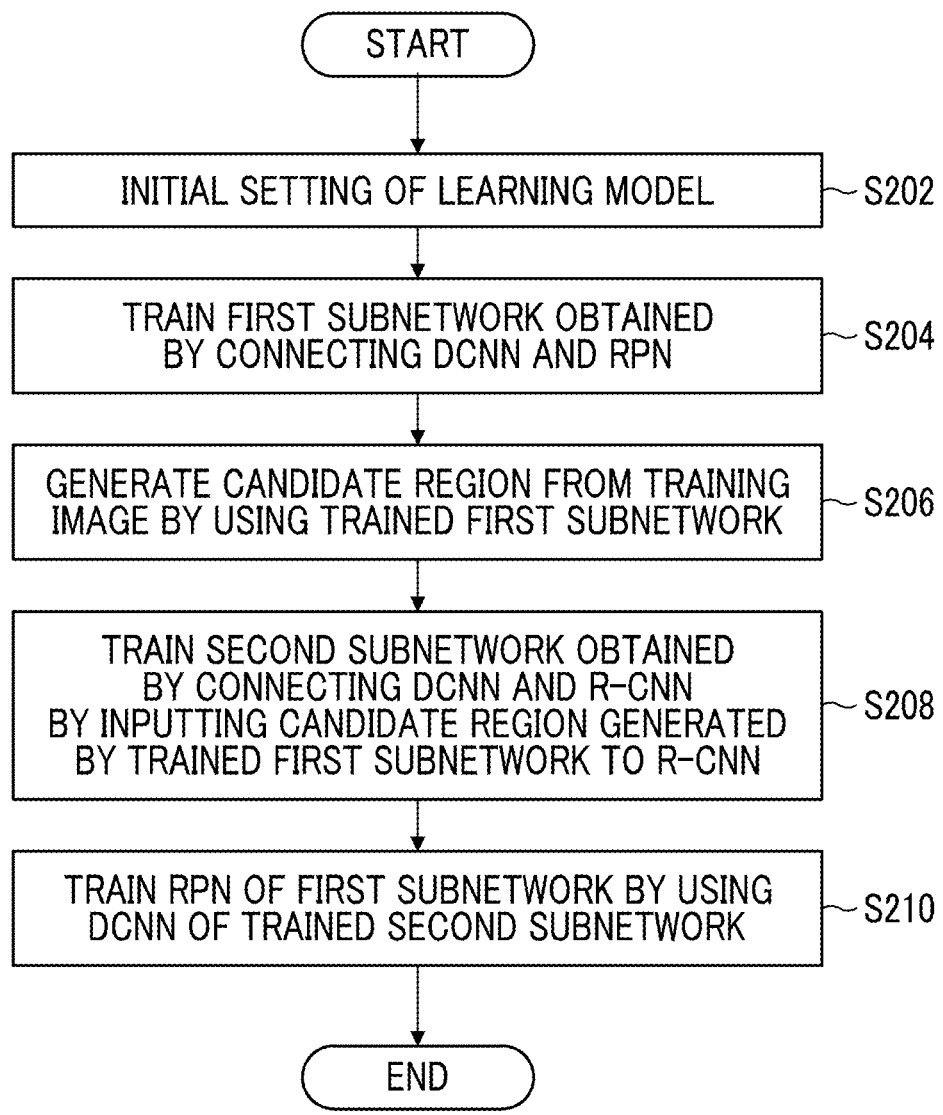
FIG. 18 is a flowchart showing an example of a learning method of the learning model in the linear structure extraction device according to the present embodiment.

FIG. 18 is a flowchart showing an example of the learning method of the learning model 52 in the linear structure extraction device 50 according to the present embodiment. The processing shown in FIG. 18 is executed by the calculation system configured by using one or a plurality of computers functioning as the learning device 100. The calculation system executes the processing of each step in accordance with a program stored on a computer-readable medium. The calculation system used for the machine learning may be the same system as the calculation system which constitutes the linear structure extraction device 50, a different system, or a system that shares a part of elements.

In step S202 of FIG. 18, the learning device 100 performs initial setting of the learning model 52. Here, the initial setting of the learning model 52 having the network structure shown in FIG. 13 is performed. The parameters of each network of the DCNN 411, the RPN 412, and the R-CNN 423 are set to initial values. A part of the parameters may be learned parameters obtained by learning in advance.

In step S204 of FIG. 18, the learning device 100 trains the model of the first subnetwork 410 obtained by connecting the DCNN 411 and the RPN 412. In step S204, the parameters of the networks of the DCNN 411 and the RPN 412 are updated. Note that the learning device 100 can acquire the learning data in units of mini-batch including the plurality of pieces of learning data LD(i), and the optimizer 114 can perform the parameter updating processing in units of mini-batch.

Then, in step S206, the learning device 100 generates the candidate region from the training image by using the trained first subnetwork 410.

In step S208, the learning device 100 inputs the candidate region generated by the trained first subnetwork 410 to the R-CNN 423 and trains the model of the second subnetwork 420 in which the DCNN 411 and the R-CNN 423 are connected. In step S208, the parameters of the networks of the DCNN 411 and the R-CNN 423 are updated.

In step S210, the learning device 100 retrains the RPN 412 of the trained first subnetwork 410 by using the DCNN 411 of the trained second subnetwork 420.

After step S210, the learning device 100 may return to step S206 to repeat training, or may terminate the flowchart of FIG. 18 based on a predetermined learning termination condition.

The learning termination condition may be determined based on the error value or may be determined based on the number of updates of parameter. As the method based on the error value, for example, the learning termination condition may be that the error converges within a specified range. As the method based on the number of updates, for example, the learning termination condition may be that the number of updates reaches the specified number of times.

Application to Three-Dimensional Image

Although the description has been made so far with the two-dimensional image as an example, the matters described about the two-dimensional image can be extended and applied to the processing of the three-dimensional image. The replacement in a case of expanding from two dimensions to three dimensions is, for example, as follows.

The "pixel" can be paraphrased as a "voxel". The "rectangle" can be paraphrased as a "rectangular parallelepiped". A "cube" can be understood as a kind of a "rectangular parallelepiped". The two-dimensional xy coordinate can be paraphrased as a three-dimensional xyz coordinate. The "aspect ratio" of the rectangle can be paraphrased as a "ratio of three sides" of the rectangular parallelepiped. The anchor can be understood as a reference shape region having predetermined shape and size, and in a case of the three-dimensional image, the rectangular parallelepiped having a three-dimensional shape is used. That is, the reference shape region of the anchor for the two-dimensional image is a rectangular region, whereas the reference shape region of the anchor for the three-dimensional image is a rectangular parallelepiped region.

Example of Hardware Configuration of Computer

Figure 19:
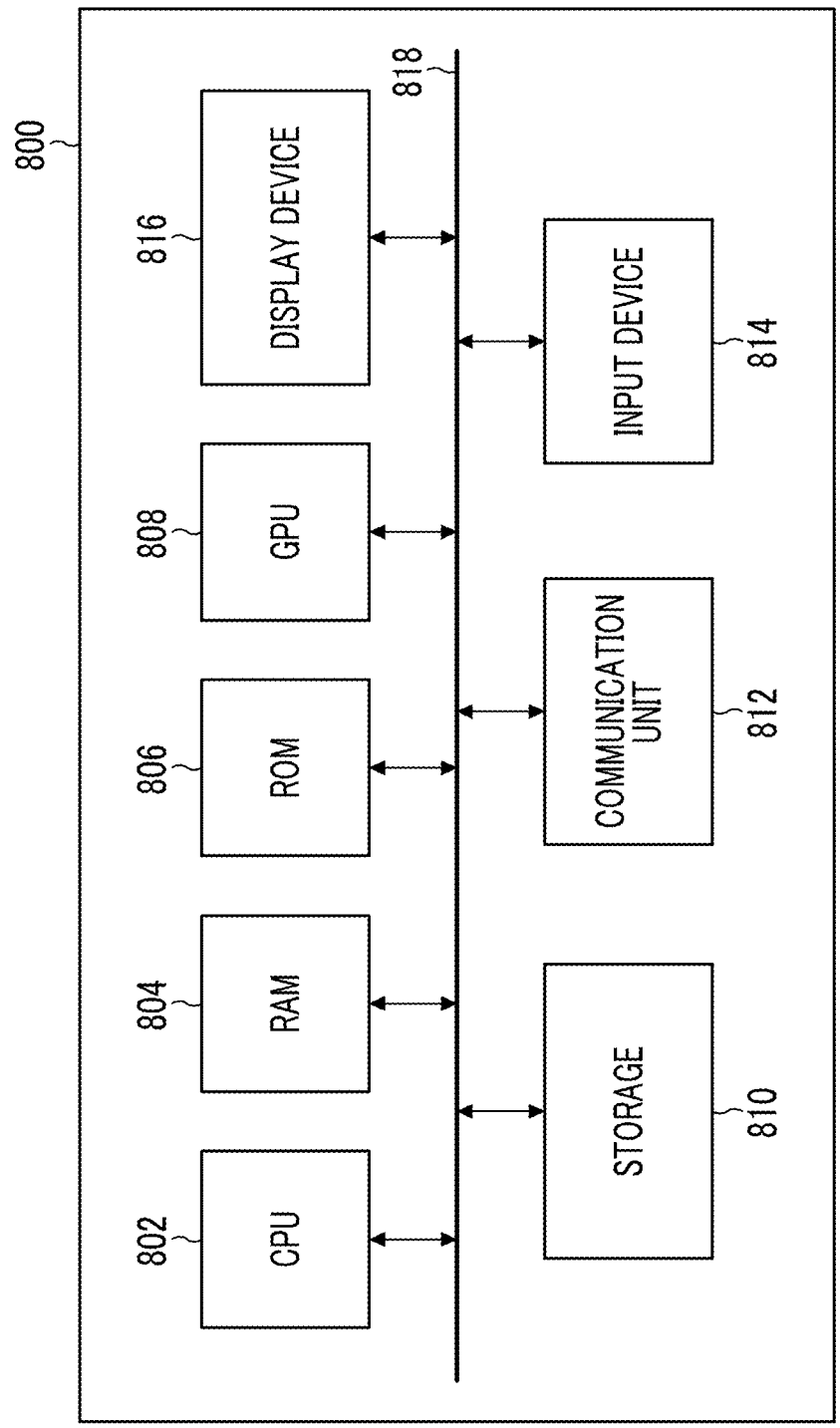
FIG. 19 is a block diagram showing an example of a hardware configuration of a computer.

FIG. 19 is a block diagram showing an example of a hardware configuration of the computer. A computer 800 may be a personal computer, a workstation, or a server computer. The computer 800 can be used as a device having a part or all of any one of the linear structure extraction device 50, the learning device 100, or the learning data storage unit 150, which have been described, or a device having a plurality of functions thereof.

The computer 800 comprises a central processing unit (CPU) 802, a random access memory (RAM) 804, a read only memory (ROM) 806, a graphics processing unit (GPU) 808, a storage 810, a communication unit 812, an input device 814, a display device 816, and a bus 818. Note that the graphics processing unit (GPU) 808 need only be provided, if necessary.

The CPU 802 reads out various programs stored in the ROM 806, the storage 810, or the like, and executes various pieces of processing. The RAM 804 is used as a work region of the CPU 802. Further, the RAM 804 is used as a storage unit that temporarily stores the read program and various pieces of data.

The storage 810 is configured to include, for example, a hard disk apparatus, an optical disk, a magneto-optical disk, or a semiconductor memory, or a storage device configured by using an appropriate combination thereof. The storage 810 stores various programs, pieces of data, or the like required for linear structure extraction processing and/or learning processing. The program stored in the storage 810 is loaded into the RAM 804, and the CPU 802 executes the program, so that the computer 800 functions as means for performing various pieces of processing specified by the program.

The communication unit 812 is an interface that performs communication processing with an external device by wire or wirelessly, and performs exchange of the information with the external device. The communication unit 812 can have the role of the image reception unit that receives the input of the image.

The input device 814 is an input interface that receives various operation inputs with respect to the computer 800. For example, the input device 814 may be a keyboard, a mouse, a touch panel, other pointing devices, a voice input device, or an appropriate combination thereof.

The display device 816 is an output interface on which various types of information are displayed. For example, the display device 816 may be a liquid crystal display, an organic electro-luminescence (OEL) display, a projector, or an appropriate combination thereof.

About Program Causing Computer to Operate

The program that causes the computer to realize a part or all of at least one processing function of the linear structure extraction function or the learning function described in the embodiment can be recorded on the computer-readable medium which is the tangible non-temporary information storage medium such as the optical disk, the magnetic disk, the semiconductor memory, or other objects, and the program can be provided through the information storage medium.

Further, instead of the aspect in which the program is stored in such a tangible non-temporary information storage medium and provided, the program signal can be provided as a download service by using the electric telecommunication line such as the Internet.

Further, a part or all of at least one processing function of the linear structure extraction function or the learning function described in the embodiment is provided as an application server, and services that provide the processing function can be performed through the electric telecommunication line.

About Hardware Configuration of Each Processing Unit

The hardware structures of the processing units that execute various pieces of processing, such as the first neural network 41, the DCNN 411, the RPN 412, the second neural network 42, the R-CNN 423, which are in FIG. 4, the data acquisition unit 102, the learning model 52, the first error calculation unit 110, the second error calculation unit 112, and the optimizer 114, which are in FIG. 17, are various processors as shown below, for example.

The various processors include the CPU that is a general-purpose processor executing the program and functioning as the various processing units, the GPU that is a processor specialized in the image processing, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of these various processors or may be configured by two or more processors of the same type or different types. For example, one processing unit may be configured by a plurality of FPGAs, a combination of the CPU and the FPGA, or a combination of the CPU and the GPU. Alternatively, a plurality of processing units may be configured by one processor. As an example of the configuration of a plurality of processing units with one processor, first, as represented by a computer such as a client or a server, there is a form in which one processor is configured by a combination of one or more CPUs and the software and the processor functions as a plurality of processing units. Second, as represented by a system on chip (SoC), there is a form in which a processor is used in which the function of the entire system including a plurality of processing units is realized by a single integrated circuit (IC) chip. As described above, the various processing units are configured by one or more of the above various processors as a hardware structure.

Furthermore, the hardware structure of these various processors is, more specifically, an electric circuit (circuitry) in which the circuit elements such as semiconductor elements are combined.

Effect of Embodiment (1) According to the present embodiment, it is possible to extract the linear structure from the image.

(2) According to the present embodiment, the element points of the linear structure are directly detected, and thus it is easy to reconstruct the graph structure.

(3) According to the present embodiment, the correct to each training image is defined by the data indicating the positional information of the center line, it is easy to create the learning data.

Other Application Examples

The technique of the linear structure extraction processing according to the present disclosure is not limited to the CT image, and can be applied to various three-dimensional tomographic images. For example, the learning method may be applied to a magnetic resonance (MR) image acquired by a magnetic resonance imaging (MRI) device, a positron emission tomography (PET) image acquired by a PET device, an optical coherence tomography (OCT) image acquired by an OCT device, a three-dimensional ultrasound image acquired by a three-dimensional ultrasound imaging device, and the like.

Further, the technique of the linear structure extraction processing according to the present disclosure is limited to the three-dimensional tomographic image, and can be applied to various two-dimensional images. For example, the image, which is the processing target, may be a two-dimensional X-ray image. Further, the technique of the linear structure extraction processing according to the present disclosure is not limited to the medical image, and can be applied to various images such as a normal camera image. For example, the technique of the present disclosure can be applied in a case in which the crack is detected from the image of the building or the like handled in Gahayun Suh, Young-Jin Cha "Deep faster R-CNN-based automated detection and localization of multiple types of damage" Sensors and Smart Structures Technologies for Civil, Mechanical, and Aerospace Systems 2018.

Modification Example

[1] The type of the anchor may be one type depending on the shape and/or the size of the target object to be detected.

[2] It is also possible to adopt a form in which the calculation of the deformation magnification of the anchor is not performed in the RPN 412, such as a case in which the size of the target object does not matter.

Others

The matters described in the configuration or the modification example described in the embodiment described above can be used in combination as appropriate, and a part of the matters can be replaced. It is needless to say that the present invention is not limited to the embodiment described above and various modifications can be made without departing from the spirit of the present invention.

EXPLANATION OF REFERENCES

40: Faster R-CNN
41: first neural network
42: second neural network
50: linear structure extraction device
52: learning model
71: first anchor
72: second anchor
81, 82, 83: anchor
100: learning device
102: data acquisition unit
110: first error calculation unit
112: second error calculation unit
114: optimizer
150: learning data storage unit
410: first subnetwork
411: DCNN
412: RPN
414, 416, 417, 418: convolutional layer
420: second subnetwork
423: R-CNN
424: ROI pooling layer
426, 427: fully bonded layer
428: softmax layer
800: computer
810: storage
812: communication unit
814: input device
816: display device
818: bus
A1, A2, A3: anchor
BV: blood vessel
Car: coronary artery route
CLbv: center line
CP, CP34: center coordinate
NP, NP34: closest point
Nd: node
Eg: edge
HVR1: image
HVR2: image
IMipt: input image
FM: feature map
RP: candidate region
LD(i): learning data
PLQ: plaque
px: pixel
pxfm: pixel
u: unit
S50 to S58: step of linear structure extraction processing
S61 to S67: step of candidate region generation processing
S202 to S210: step of learning processing

What is claimed is:

1. A linear structure extraction device that extracts element points which constitute a linear structure from an image, the device comprising a processor, wherein the processor implements: a learning model that is learned to receive an input of the image and output, as a prediction result, one or more element points which constitute the linear structure from the image, wherein the learning model includes a first processing module that receives the image and generates a feature map representing a feature amount of the image by convolution processing, and a second processing module that calculates a shift amount from a unit center point to the element point of the linear structure closest to the unit center point, for each unit obtained by dividing the feature map into a plurality of the units including regions having a predetermined size in a grid pattern, wherein the second processing module disposes anchors, which are one or more reference shape regions having predetermined shape and size, in each of the units, and performs, for each unit, the convolution processing by using the feature amount at a position of the unit to calculate the shift amount for moving an anchor center point of the anchor to a closest point, which is the element point of the linear structure closest to the anchor center point, and a score for determining whether or not the linear structure is present in the anchors.

2. The linear structure extraction device according to claim 1, wherein the reference shape region is a rectangular region in a case in which the image is a two-dimensional image, and is a rectangular parallelepiped region in a case in which the image is a three-dimensional image.

3. The linear structure extraction device according to claim 1, wherein the linear structure is a representative line of a region having a thickness in the image, and a plurality of the anchors having different sizes are used in accordance with the thickness of the region having the thickness.

4. The linear structure extraction device according to claim 3,
wherein the region having the thickness is a tubular structure, and
the representative line is a center line along a route of the tubular structure.

5. The linear structure extraction device according to claim 1, wherein the linear structure is a representative line of a region having a thickness in the image, and the second processing module is learned to change the size of the anchor in accordance with the thickness of the region having the thickness, which is a target.

6. The linear structure extraction device according to claim 1, wherein the linear structure is a representative line of a region having a thickness in the image, and the second processing module is learned to calculate, for each anchor, a deformation magnification of the anchor in a direction of at least one side of the anchor in accordance with the thickness of the region having the thickness around the closest point.

7. The linear structure extraction device according to claim 1,
wherein each of the first processing module and the second processing module is configured by a neural network,
the first processing module is configured by a convolutional neural network including a plurality of convolutional layers, and
the second processing module includes a convolutional layer different from that of the first processing module and is configured by a region proposal network that predicts a candidate region including the linear structure from the feature map.

8. The linear structure extraction device according to claim 1, further comprising:
a third processing module that is learned to perform classification of each point with respect to the element points of the linear structure predicted by the second processing module.

9. The linear structure extraction device according to claim 8, wherein a class classified by the third processing module includes at least one of a root, a branch, a tip, or a point on a twig in a tree structure of graph theory.

10. The linear structure extraction device according to claim 8,
wherein the linear structure is a center line along a route of a blood vessel, and
a class classified by the third processing module includes a specific anatomical name in a vascular structure.

11. The linear structure extraction device according to claim 8,
wherein the linear structure is a center line along a route of a trachea, and
a class classified by the third processing module includes a specific anatomical name in a tracheal structure.

12. The linear structure extraction device according to claim 8,
wherein the third processing module is configured by a neural network, and
the third processing module includes
a region-of-interest pooling layer that cuts out a local image of the anchor including the element point predicted by the second processing module from the feature map and deforms the local image to a fixed size, and
at least one of a convolutional layer or a fully bonded layer to which the local image deformed into the fixed size is input.

13. A linear structure extraction method that extracts element points which constitute a linear structure from an image, the method comprising: by using a learning model implemented by a processor that is learned to receive an input of the image and output, as a prediction result, one or more element points which constitute the linear structure from the image, receiving the input of the image to the learning model; generating a feature map representing a feature amount of the image by performing convolution processing on the input image by using a first processing module; and dividing the feature map into a plurality of units including regions having a predetermined size in a grid pattern and calculating, for each unit, a shift amount from a unit center point to the element point of the linear structure closest to the unit center point by using a second processing module, wherein the second processing module disposes anchors, which are one or more reference shape regions having predetermined shape and size, in each of the units, and performs, for each unit, the convolution processing by using the feature amount at a position of the unit to calculate the shift amount for moving an anchor center point of the anchor to a closest point, which is the element point of the linear structure closest to the anchor center point, and a score for determining whether or not the linear structure is present in the anchors.

14. The linear structure extraction method according to claim 13, further comprising:
deleting, from a point cloud of a plurality of the element points predicted by the plurality of units, a part of excess element points close to each other by less than a first interval, which is half of the size of the unit as a standard, and selecting and leaving the element points at a degree of the first interval.

15. The linear structure extraction method according to claim 13,
wherein the linear structure is a representative line of a region having a thickness in the image, and
the linear structure extraction method further comprises deleting, from a point cloud of a plurality of the element points predicted by the plurality of units, a part of excess element points close to each other by less than a second interval, which is half of the thickness as a standard, and selecting and leaving the element points at a degree of the second interval.

16. The linear structure extraction method according to claim 13, further comprising:
deleting, from a point cloud of a plurality of the element points predicted by the plurality of units, an isolation point around which other points are not present within a distance of a predetermined threshold value.

17. A non-temporary computer-readable recording medium that causes a computer to execute the linear structure extraction method according to claim 13 in a case in which a command stored in the recording medium is read by the computer.

18. A system comprising a processor and a memory storing a program when executed by the processor to perform a method comprising receiving by a learned model that is learned to output, as a prediction result, one or more element points which constitute a linear structure from an input image, the model comprising, wherein the learned model comprises: a first processing module that receives the image and generates a feature map representing a feature amount of the image by convolution processing; and a second processing module that calculates a shift amount from a unit center point to the element point of the linear structure closest to the unit center point, for each unit obtained by dividing the feature map into a plurality of the units including regions having a predetermined size in a grid pattern, wherein the second processing module disposes anchors, which are one or more reference shape regions having predetermined shape and size, in each of the units, and performs, for each unit, the convolution processing by using the feature amount at a position of the unit to calculate the shift amount for moving an anchor center point of the anchor to a closest point, which is the element point of the linear structure closest to the anchor center point, and a score for determining whether or not the linear structure is present in the anchors.

19. The learned model according to claim 18,
wherein parameters of networks which configure the first processing module and the second processing module are decided by executing machine learning by using a plurality of pieces of learning data in which a training image and positional information of the linear structure included in the training image are combined.

20. The learned model according to claim 19,
wherein the linear structure is a representative line of a region having a thickness in the image, and
the learning data further includes thickness information of the region having the thickness included in the training image.

* * * * *